(12) United States Patent
Flocard et al.

(10) Patent No.: US 7,849,545 B2
(45) Date of Patent: Dec. 14, 2010

(54) CONTROL SYSTEM FOR HOSPITAL BED MATTRESS

(75) Inventors: Thierry Flocard, Montpellier (FR); Gilles Camus, Montpellier (FR); Jean-Marie Basilio, Meze (FR); Jean-Louis Viard, Grabels (FR)

(73) Assignee: Hill-Rom Industries SA, Montpellier (FR)

( * ) Notice: Subject to any disclaimer, the term of this patent is extended or adjusted under 35 U.S.C. 154(b) by 457 days.

(21) Appl. No.: 11/559,529

(22) Filed: Nov. 14, 2006

(65) Prior Publication Data

US 2008/0109964 A1  May 15, 2008

(51) Int. Cl.
*A47C 27/08* (2006.01)

(52) U.S. Cl. .................. 5/713; 5/600; 5/658

(58) Field of Classification Search ............ 5/600, 5/613, 616, 424; 292/240–242, 95
See application file for complete search history.

(56) References Cited

U.S. PATENT DOCUMENTS

| | | | |
|---|---|---|---|
| 2,719,986 A | 10/1955 | Rand | |
| 4,224,706 A | 9/1980 | Young et al. | |
| 4,394,784 A | 7/1983 | Swenson et al. | |
| 4,634,179 A | 1/1987 | Hashimoto et al. | |
| 4,638,519 A | 1/1987 | Hess | |
| 4,694,409 A | 9/1987 | Lehman | |
| 4,694,520 A | 9/1987 | Paul et al. | |
| 4,745,647 A | 5/1988 | Goodwin | |
| 4,768,249 A | 9/1988 | Goodwin | |
| 4,797,962 A | 1/1989 | Goode | |
| 4,833,457 A | 5/1989 | Graebe, Jr. | |
| 4,839,512 A | 6/1989 | Speck | |
| 4,845,323 A | 7/1989 | Beggs | |
| 4,864,671 A | 9/1989 | Evans | |
| 4,873,737 A | 10/1989 | Savenije | |
| 4,890,344 A | 1/1990 | Walker | |
| 4,896,389 A | 1/1990 | Chamberland | |
| 4,897,890 A | 2/1990 | Walker | |
| 4,907,845 A | 3/1990 | Wood | |
| 4,914,771 A | 4/1990 | Afeyan | |
| 4,944,060 A | 7/1990 | Peery et al. | |

(Continued)

FOREIGN PATENT DOCUMENTS

DE        3804961        8/1989

(Continued)

*Primary Examiner*—Michael Trettel
*Assistant Examiner*—William Kelleher
(74) *Attorney, Agent, or Firm*—Barnes & Thornburg LLP

(57) ABSTRACT

A mattress system includes a mattress, a control unit spaced from the mattress, and a connector assembly that pneumatically and electrically interconnects the control unit with the mattress. The control unit has a main housing and a plurality of user interface modules that are selectively coupleable to the control unit and that are programmed differently to provide different modes of operation for the mattress system. A pressure sensor inside the mattress detects the presence or absence of a person on the mattress. The mattress system has a bed exit alarm system that, when armed, provides a bed exit alarm if the pressure sensor in the mattress detects that a patient has exited the mattress. The connector assembly includes a dual mode connector having both electrical and pneumatic couplers and a dual lumen hose assembly that extends from the dual mode connector to the mattress.

22 Claims, 11 Drawing Sheets

U.S. PATENT DOCUMENTS

| | | | |
|---|---|---|---|
| 4,947,298 A | 8/1990 | Stephen | |
| 4,949,412 A | 8/1990 | Goode | |
| 4,949,413 A | 8/1990 | Goodwin | |
| 4,949,414 A | 8/1990 | Thomas et al. | |
| 4,951,032 A | 8/1990 | Langsam | |
| 4,953,247 A | 9/1990 | Hasty | |
| 4,986,738 A | 1/1991 | Kawasaki et al. | |
| 4,989,283 A | 2/1991 | Krouskop | |
| 4,993,920 A | 2/1991 | Harkleroad et al. | |
| 4,995,124 A | 2/1991 | Wridge, Jr. et al. | |
| 5,003,654 A | 4/1991 | Vrzalik | |
| 5,005,240 A | 4/1991 | Vrzalik | |
| 5,010,772 A | 4/1991 | Bourland et al. | |
| 5,020,176 A | 6/1991 | Dotson | |
| 5,022,110 A | 6/1991 | Stroh | |
| 5,035,016 A | 7/1991 | Mori et al. | |
| 5,044,029 A | 9/1991 | Vrzalik | |
| 5,052,067 A | 10/1991 | Thomas et al. | |
| 5,062,167 A | 11/1991 | Thomas et al. | |
| 5,070,560 A | 12/1991 | Wilkinson | |
| 5,073,999 A | 12/1991 | Thomas et al. | |
| 5,090,077 A | 2/1992 | Caden et al. | |
| 5,095,568 A | 3/1992 | Thomas et al. | |
| 5,103,519 A | 4/1992 | Hasty | |
| 5,117,518 A | 6/1992 | Schild | |
| 5,140,309 A | 8/1992 | Gusakov | |
| 5,152,021 A | 10/1992 | Vrzalik | |
| 5,170,364 A | 12/1992 | Gross et al. | |
| 5,184,112 A | 2/1993 | Gusakov | |
| 5,189,742 A | 3/1993 | Schild | |
| 5,251,349 A | 10/1993 | Thomas et al. | |
| 5,253,656 A | 10/1993 | Rincoe et al. | |
| 5,267,364 A | 12/1993 | Volk | |
| 5,269,030 A | 12/1993 | Pahno et al. | |
| 5,276,432 A | 1/1994 | Travis | |
| 5,325,551 A | 7/1994 | Tappel et al. | |
| 5,393,935 A | 2/1995 | Hasty et al. | |
| 5,393,938 A | 2/1995 | Bumbalough | |
| 5,396,671 A | 3/1995 | Stacy | |
| 5,438,721 A | 8/1995 | Pahno et al. | |
| 5,483,709 A | 1/1996 | Foster et al. | |
| 5,487,196 A | 1/1996 | Wilkinson et al. | |
| 5,493,742 A | 2/1996 | Klearman | |
| D368,475 S | 4/1996 | Scott | |
| 5,509,154 A | 4/1996 | Shafer et al. | |
| 5,509,155 A | 4/1996 | Zigarac et al. | |
| 5,539,942 A | 7/1996 | Melou | |
| 5,542,136 A | 8/1996 | Tappel | |
| 5,554,835 A | 9/1996 | Newham | |
| 5,560,057 A | 10/1996 | Madsen et al. | |
| 5,560,374 A | 10/1996 | Viard | |
| 5,584,084 A | 12/1996 | Klearman et al. | |
| 5,586,346 A | 12/1996 | Stacy et al. | |
| 5,586,347 A | 12/1996 | Frischknecht | |
| 5,594,963 A | 1/1997 | Berkowitz | |
| 5,600,108 A | 2/1997 | Newham | |
| 5,603,133 A | 2/1997 | Vrzalik | |
| 5,606,754 A | 3/1997 | Hand et al. | |
| 5,606,756 A | 3/1997 | Price | |
| 5,611,096 A | 3/1997 | Bartlett et al. | |
| 5,611,772 A | 3/1997 | Fujimoto et al. | |
| 5,623,760 A | 4/1997 | Newham | |
| 5,630,238 A | 5/1997 | Weismiller et al. | |
| 5,633,627 A | 5/1997 | Newham | |
| 5,640,145 A | 6/1997 | Newham | |
| 5,652,484 A | 7/1997 | Shafer et al. | |
| 5,654,694 A | 8/1997 | Newham | |
| 5,664,270 A | 9/1997 | Bell et al. | |
| 5,699,570 A | 12/1997 | Wilkinson et al. | |
| 5,701,622 A * | 12/1997 | Biggie et al. | 5/713 |
| 5,704,084 A | 1/1998 | Evans et al. | |
| 5,729,853 A | 3/1998 | Thompson | |
| 5,741,032 A * | 4/1998 | Chaput | 292/202 |
| 5,755,000 A | 5/1998 | Thompson | |
| 5,774,917 A | 7/1998 | Liu | |
| 5,780,798 A | 7/1998 | Hall-Jackson | |
| 5,794,288 A | 8/1998 | Soltani et al. | |
| 5,796,059 A | 8/1998 | Boon | |
| 5,815,864 A | 10/1998 | Sloop | |
| 5,844,488 A | 12/1998 | Musick | |
| 5,848,450 A | 12/1998 | Oexman et al. | |
| 5,882,349 A | 3/1999 | Wilkerson et al. | |
| 5,890,245 A | 4/1999 | Klearman et al. | |
| 5,903,941 A | 5/1999 | Shafer et al. | |
| 5,926,884 A | 7/1999 | Biggie et al. | |
| 5,944,066 A | 8/1999 | Viard | |
| 5,947,168 A | 9/1999 | Viard | |
| 5,963,997 A | 10/1999 | Hagopian | |
| 5,970,550 A | 10/1999 | Gazes | |
| 5,983,428 A | 11/1999 | Hannagan | |
| 5,983,429 A | 11/1999 | Stacy et al. | |
| 5,990,799 A | 11/1999 | Boon et al. | |
| 6,009,580 A | 1/2000 | Caminade et al. | |
| 6,012,186 A | 1/2000 | Soltani et al. | |
| 6,014,784 A | 1/2000 | Taylor et al. | |
| 6,021,800 A | 2/2000 | Schild et al. | |
| 6,025,782 A | 2/2000 | Newham | |
| 6,034,526 A | 3/2000 | Montant et al. | |
| 6,036,660 A | 3/2000 | Toms | |
| 6,037,723 A | 3/2000 | Shafer et al. | |
| 6,047,424 A | 4/2000 | Osborne et al. | |
| 6,058,537 A | 5/2000 | Larson | |
| 6,058,538 A | 5/2000 | Chapman et al. | |
| 6,061,855 A | 5/2000 | Flick | |
| 6,073,291 A | 6/2000 | Davis | |
| 6,079,068 A | 6/2000 | Viard | |
| 6,079,070 A | 6/2000 | Flick | |
| 6,094,762 A | 8/2000 | Viard et al. | |
| 6,098,222 A | 8/2000 | Hand et al. | |
| 6,108,843 A | 8/2000 | Suzuki et al. | |
| 6,111,509 A | 8/2000 | Holmes | |
| 6,115,860 A | 9/2000 | Vrzalik | |
| 6,134,732 A | 10/2000 | Chapman et al. | |
| 6,145,142 A | 11/2000 | Rechin et al. | |
| 6,212,718 B1 | 4/2001 | Stolpmann et al. | |
| 6,223,369 B1 | 5/2001 | Maier et al. | |
| 6,239,706 B1 | 5/2001 | Yoshiike et al. | |
| 6,252,512 B1 | 6/2001 | Riley | |
| 6,282,737 B1 | 9/2001 | Vrzalik | |
| 6,297,738 B1 | 10/2001 | Newham | |
| 6,307,476 B1 | 10/2001 | Smith et al. | |
| 6,353,950 B1 | 3/2002 | Bartlett et al. | |
| 6,378,152 B1 | 4/2002 | Washburn et al. | |
| 6,385,803 B1 | 5/2002 | Viard | |
| 6,412,129 B1 | 7/2002 | Wu | |
| 6,417,777 B2 | 7/2002 | Fitzgerald et al. | |
| 6,421,859 B1 | 7/2002 | Hicks et al. | |
| 6,441,742 B1 | 8/2002 | Lovely et al. | |
| 6,483,264 B1 | 11/2002 | Shafer et al. | |
| 6,487,739 B1 | 12/2002 | Harker | |
| 6,544,200 B1 | 4/2003 | Smith et al. | |
| 6,583,727 B2 | 6/2003 | Nunome | |
| 6,584,628 B1 * | 7/2003 | Kummer et al. | 5/615 |
| 6,591,437 B1 | 7/2003 | Phillips | |
| 6,646,556 B1 | 11/2003 | Smith et al. | |
| 6,686,711 B2 | 2/2004 | Rose et al. | |
| 6,687,937 B2 | 2/2004 | Harker | |
| 6,698,046 B1 | 3/2004 | Wu | |
| 6,701,558 B2 | 3/2004 | VanSteenburg | |
| 6,721,980 B1 | 4/2004 | Price et al. | |
| 6,727,445 B2 | 4/2004 | Cullinan et al. | |
| 6,730,115 B1 | 5/2004 | Heaton | |
| 6,745,996 B1 | 6/2004 | Guthrie | |
| 6,759,607 B2 | 7/2004 | Engler | |

| | | |
|---|---|---|
| 6,782,574 B2 | 8/2004 | Totton et al. |
| 6,784,797 B2 | 8/2004 | Smith et al. |
| 6,789,284 B2 | 9/2004 | Kemp |
| 6,813,790 B2 | 11/2004 | Flick et al. |
| 6,820,640 B2 | 11/2004 | Hand et al. |
| 6,829,796 B2 * | 12/2004 | Salvatini et al. ............ 5/713 |
| 6,855,158 B2 | 2/2005 | Stolpmann |
| 6,877,178 B2 | 4/2005 | Chapman et al. |
| 6,892,405 B1 | 5/2005 | Dimitriu et al. |
| 6,897,781 B1 | 5/2005 | Cooper et al. |
| 6,907,633 B2 | 6/2005 | Paolini et al. |
| 6,917,293 B2 | 7/2005 | Beggs |
| 6,928,681 B1 | 8/2005 | Stacy |
| 6,943,694 B1 | 9/2005 | Ellis |
| 6,987,232 B2 | 1/2006 | Smith et al. |
| 6,998,986 B2 | 2/2006 | Smith |
| 7,030,764 B2 | 4/2006 | Smith et al. |
| 7,036,171 B2 | 5/2006 | Wu |
| 2001/0001237 A1 | 5/2001 | Stroda et al. |
| 2002/0067273 A1 | 6/2002 | Jaques et al. |
| 2002/0073489 A1 | 6/2002 | Totton et al. |
| 2002/0189924 A1 | 12/2002 | Cullinan et al. |
| 2002/0196148 A1 | 12/2002 | Nunome |
| 2003/0046762 A1 | 3/2003 | Stolpmann |
| 2003/0063010 A1 | 4/2003 | Smith et al. |
| 2003/0073936 A1 | 4/2003 | Raisanen |
| 2003/0145386 A1 | 8/2003 | Kemp |
| 2004/0031103 A1 | 2/2004 | Wyatt et al. |
| 2004/0261182 A1 | 12/2004 | Biggie et al. |
| 2005/0022308 A1 | 2/2005 | Totton et al. |
| 2005/0035871 A1 * | 2/2005 | Dixon et al. ............ 340/686.1 |
| 2005/0081300 A1 | 4/2005 | O'Reagan et al. |
| 2006/0258964 A1 * | 11/2006 | Biondo et al. ............ 601/152 |

FOREIGN PATENT DOCUMENTS

| | | |
|---|---|---|
| EP | 0 218 301 A2 | 4/1987 |
| EP | 0 676 158 A1 | 10/1995 |
| WO | WO 2004091463 A2 * | 10/2004 |

* cited by examiner

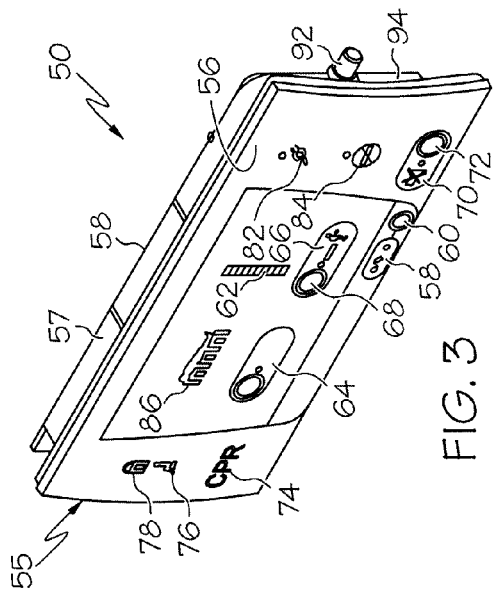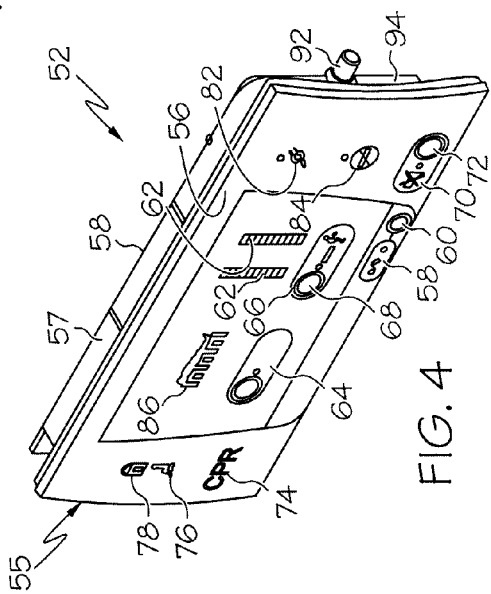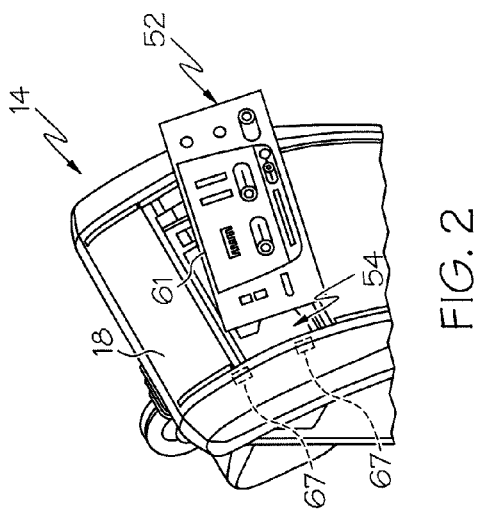

CONTROL SYSTEM FOR HOSPITAL BED MATTRESS

BACKGROUND OF THE INVENTION

The present disclosure relates to hospital bed mattresses and particularly, to control systems for hospital bed mattresses in which portions of the control systems may control inflation of one or more air bladders included in the mattresses and portions of the control systems may control bed exit alarms. The present disclosure also relates to hose assemblies that interconnect control units with associated mattresses.

Hospitals use a variety of different mattress types to support patients having different medical needs. Some patients benefit from being supported on alternating pressure mattresses or rotation therapy mattress. Other patients may not need to be supported on these types of mattresses having dynamic therapies, but rather, so-called static air mattresses that simply operate to provide a relatively low interface pressure may be suitable for such patients. To address these various mattress requirements, manufacturers may market a number of mattress products, each with its own particularized therapeutic function, or may market mattresses that have control units allowing users to program or select different modes of operation. It can be expensive for hospitals or other healthcare institutions to purchase a large number of mattresses, each having its own dedicated therapeutic functionality. However, mattresses allowing user selectable functionality introduce the possibility that users may inadvertently configure the mattress with the wrong type of therapy or operation among the plurality of the available therapies.

It is sometimes desirable for patients to remain in bed and, in such situations, hospitals are interested in having some type of bed exit alarm for these patients to provide an alarm or alarm signal indicating that the patient has exited, or is about to exit, the bed. Some bed frames have built-in bed exit alarm systems, oftentimes using the load cells of a weigh scale system, to determine the presence or absence of a patient on the bed and triggering a bed exit alarm when a threshold amount of weight is determined to have been removed from the bed. The addition of a weigh scale system to a bed frame adds cost and therefore, hospitals purchase many bed frames without the weigh scale system option and consequently, therefore, without any bed exit alarm capability. Separate bed exit systems having strips or mats that are placed on top of a mattress and underneath a patient are known in the art, but such strips or mats may result in increased interface pressure on the patient and thus, may compromise the ability of the mattress to support the patient with relatively low interface pressure.

SUMMARY OF THE INVENTION

The present invention comprises an apparatus or system having one or more of the features recited in the appended claims and/or one or more of the following features, which alone or in any combination may comprise patentable subject matter:

A mattress system may comprise a mattress having at least one inflatable bladder and a control unit. The control unit may comprise a main housing, a source of pneumatic pressure carried by the main housing and operable to inflate the at least one inflatable bladder, and a plurality of user interface modules that are coupleable to the main housing. Each user interface module may be programmed to control inflation of the at least one air bladder differently in at least one operational mode of each of the plurality of user interface modules.

The user interface modules may include an alternating pressure module and a continuous low pressure module. Additionally or alternatively, the user interface modules may include a rotation therapy module. One or more the user interface modules may be programmed to provide two different types of therapies. Each of user interface modules may have user inputs that are used to change a mode of operation of the associated user interface module. One or more of the user interface modules may be programmed to provide a maximum inflation mode in which the at least one inflatable bladder is inflated to a maximum threshold pressure which renders the at least one air bladder suitably hard for patient transfer. One or more of the user interface modules may include at least one visual indicator that is operable to provide visual indication of the operational status of the mattress system.

The control unit may have a latch coupled to the main housing and movable between a locked position in which a selected one of the plurality of user interface modules is locked to the main housing and an unlocked position in which the selected one of the plurality of user interface modules is detachable from the main housing. The latch may have a hook and each of the user interface modules may have a post that is captured by the hook when the associated user interface module is locked to the main housing by the latch. The main housing may have at least one slot and each of the plurality of interface modules may have at least one tab that is received in the slot provided in the main housing when the associated user interface module is coupled to the housing.

Each of the user interface modules may comprise a main body. The post and the at least one tab of each of the plurality of user interface modules may be located on opposite ends of the associated user interface modules. The post and the at least one tab of each of the plurality of user interface modules may extend away from the associated main body in opposite directions.

The main housing of the control unit may have a recess into which each of the user interface modules is insertable. The control unit may include a first electrical connector coupled to the main housing. Each of the user interface modules may include a second electrical connector that automatically mates with the first electrical connector upon insertion of the user interface module into the recess of the main housing.

At least one of the plurality of user interface modules may have a lockout switch that is usable to lockout at least one operational mode of the associated user interface module. The lockout switch may be located adjacent a surface, such as a back surface, of the associated user interface module that is inaccessible to a user when the associated user interface module is coupled to the main housing. The lockout switch may be used to lockout the maximum inflation mode of the associated user interface module.

One or more of the plurality of user interface modules may include inputs that are engageable to enable a bed exit alarm system of the control unit. The bed exit alarm system may receive an input signal from the mattress indicative of a pressure sensed by a pressure sensor situated in an interior region of the surface.

The source of pneumatic pressure of the control unit may comprise an air compressor within a noise-dampening housing that is situated within an interior region of the main housing. The noise-dampening housing may have an air chamber that serves as a pressure reservoir which stabilizes air flow to the at least one air bladder of the mattress.

The mattress may at least one valve located within an interior region of the mattress. The valve may be opened and closed to control pressure in the at least one inflatable bladder in a manner dictated by the programming of the selected user interface module that is coupled to the main housing. The mattress may have at least one pressure sensor situated within an interior region of the mattress and an output signal from the at least one pressure sensor may be communicated to the selected user interface module that is coupled to the main housing. At least one cardiopulmonary resuscitation (CPR) input may be coupled to the mattress and may be movable mechanically to deflate the at least one air bladder of the surface. Movement of the CPR input may result in a CPR signal being communicated to the selected user interface module that is coupled to the main housing. The selected user interface module may deactivate operation of the source of pneumatic pressure in response to receiving the CPR signal.

The control unit may have circuitry that receives a signal from the mattress which is indicative of a pressure sensed by a pressure sensor situated within an interior region of the mattress. The circuitry may use the signal to establish at least one target pressure to which the at least one inflatable bladder is controlled. The circuitry may also use the signal to determine whether to activate a bed exit alarm. The bed exit alarm may comprise a flashing light that is carried by the control unit. Alternatively or additionally, the bed exit alarm may comprise a sound-producing device, such as a speaker or buzzer, carried by the control unit.

The pressure sensor may comprise a bag filled with silicon oil. The mattress comprises an inflatable underlay having a space that receives the bag filled with silicon oil. The at least one inflatable bladder of the mattress may comprise at least one inflatable layer that overlies the pressure sensor. The at least one inflatable layer may comprise first and second inflatable layers that overlie the pressure sensor. The first inflatable layer may comprise a plurality of laterally extending air bladders, at least two of which are inflatable to different pressures. The second inflatable layer may extend approximately the full length of the mattress and may be inflatable to a single target pressure.

The mattress may have one or more foam layers, blocks, pads, and/or one or more other non-inflatable support elements in lieu of, or in addition to, the at least one inflatable bladder. Accordingly, the mattress may have no inflatable bladders at all. A pressure sensor comprising an enclosure containing a liquid, such as a bag filled with silicon oil, may be used as part of a bed exit alarm system in such a foam mattress. With regard to mattresses lacking any inflatable bladders, the control unit may be omitted and the circuitry and sound-producing device of the bed exit alarm system may be included within, or coupled directly to, the mattress itself. In other embodiments, some or all of the circuitry and sound producing device of the bed exit alarm system may be situated in a housing or module that is spaced from the mattress and that is coupled to the pressure sensor via one or more electrical lines, or even wirelessly for that matter.

The mattress may have at least one electrical component situated within an interior region of the mattress, a first pneumatic port in communication with the at least one inflatable bladder of the mattress, and a first electrical connector in communication with the at least one electrical component. The circuitry of the control unit may be programmed to control the manner in which the at least one inflatable bladder is inflated. The circuitry may also include a second electrical connector and the control unit may include a second pneumatic port in communication with the source of pneumatic pressure.

A connector assembly may be provided to pneumatically connect the first pneumatic port with the second pneumatic port and to electrically connect the first electrical connector with the second electrical connector. The connector assembly may include a pneumatic line, at least one electrical line, and a dual mode plug configured to permit connection of the pneumatic line with the second pneumatic connector substantially simultaneously with connection of the at least one electrical line with the second electrical connector.

The connector assembly may include a dual lumen hose having side-by-side first and second lumens. The first lumen serves as the pneumatic line for communication of pneumatic pressure from the second pneumatic port of the control unit to the at first pneumatic port of the mattress and the second lumen serves as an electrical conduit through which the at least one electrical line is routed. A first end of the dual lumen hose may be coupled to the dual mode plug. The connector assembly may have a pneumatic coupler mounted to the first lumen at a second end of the dual lumen hose. The least one electrical line may extend beyond the second lumen at the second end of the dual lumen hose.

The dual mode plug may include a plug housing and at least one latch member coupled to the plug housing. The at least one latch member may be movable between a first position locking the dual mode plug to the main housing of the control unit and a second position unlocking the dual mode plug for detachment from the main housing of the control unit. The at least one latch member may be spring-biased toward the first position. The at least one latch member may comprise a pair of latch members, each situated on an opposite side of the plug housing. The plug housing may include a pair of recesses and at least a portion of each latch member may be received within a respective one of the pair of recesses. The pair of latch members may be movable toward the plug housing to move the pair of latch members between the respective first and second positions.

The dual mode plug may include a front wall. A pneumatic coupler may extend away from the front wall and an electrical coupler may extend away from the front wall. The pneumatic coupler may be configured to mate with the second pneumatic port of the control unit and the electrical coupler may be configured to mate with the second electrical connector of the control unit. The pneumatic coupler may be formed integrally with the front wall of the dual mode plug and the front wall of the dual mode plug may have an aperture through which the electrical coupler extends. The dual mode plug may include a check valve in communication with the pneumatic coupler.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 2 is a perspective view of the control unit of FIG. 1 showing a first user interface module being removed from a recess formed in main housing of the control unit;

FIG. 3 is a front perspective of the first user interface module of FIG. 2 showing user inputs on a front surface of the first user interface module;

FIG. 4 is a front perspective of a second user interface module that is coupleable to the main housing of the control unit in lieu of the first user interface module;

DETAILED DESCRIPTION OF THE DRAWINGS

Figure 1:
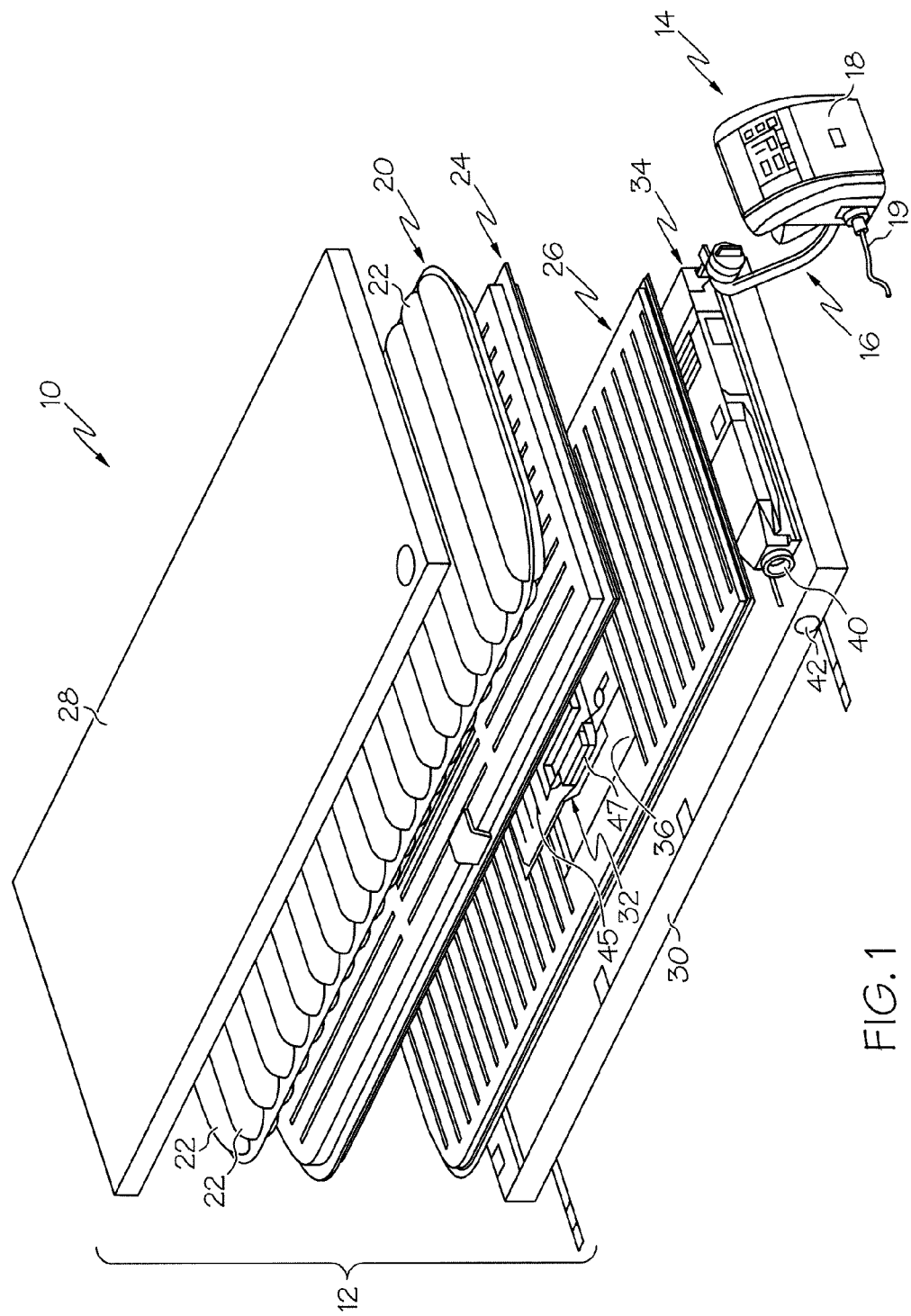
FIG. 1 is an exploded perspective view of a mattress system showing inflatable layers of a mattress of the mattress system situated between top and bottom coverlets of the mattress and showing a control unit situated near a foot end of the bottom of the coverlet coupled electrically and pneumatically by a connector assembly a technical box situated within an interior region of the mattress.

A mattress system 10 includes a mattress 12 and a control unit 14 that is spaced-apart from the mattress 12 and that is coupled pneumatically and electrically with the mattress 12 by a connector assembly 16 as shown in FIG. 1. As is discussed in greater detail below, the control unit 14 includes a plurality of user interface modules 50, 52 that are able to be selectively coupled to a main housing 18 of the control unit 14 to configure the mattress system 10 with various functionalities depending upon which of the user interface modules 50, 52 is coupled to the main housing. For example, FIG. 3 shows a user interface module 50 having a primary mode of operation that is referred to as a continuous low pressure mode and FIG. 4 shows a user interface module 52 having a primary mode of operation that is referred to as an alternating pressure therapy mode. The illustrative mattress system 10 is available commercially and is marketed as the ClinActiv™ Therapy Mattress System by Hill-Rom Company, Inc. which is an affiliate corporation of the assignee of the present application.

Illustratively, the mattress 12 includes an upper inflatable bladder layer 20 having a plurality of laterally-extending cells or bladders 22 which cooperate to define various zones of layer 20. For example, a head section zone includes the first three cells 22 of layer 20. These three cells 22 are fluidly interconnected and are illustratively regulated to the same pressure. The next ten cells 22 form a torso section zone of layer 20. Finally, a heel section zone includes the last seven cells 22 of layer 20 which are fluidly interconnected with each other and are generally regulated to a low target pressure. This target pressure is independent of the rest of the zones of the layer 20 and is regulated by electronics within the control unit 14.

When system 10 is operating in the continuous low pressure mode, as dictated by module 50, the ten cells 22 of the torso section zone are controlled to the same target pressure. However, when system 10 is operating in the alternating pressure mode, as dictated by module 52, a first group of five of the ten cells 22 of the torso section zone are deflated for a period of time while a second group of five of the ten cells 22 of the torso section zone are inflated and then, after the period of time and after a dwell time in which all ten cells 22 of the torso zone section are inflated, the first group of five of the ten cells 22 of the torso zone section are inflated for a period of time while the second group of five cells 22 of the torso section zone are deflated for a period of time. This sequence then repeats after another dwell time in which all ten cells 22 of the torso section zone are inflated. The cells 22 of the two groups of torso section zone cells 22 are arranged such that each cell of the first group is situated between adjacent cells of the second group, and vice versa, with the exception of the cells that are the head end and foot end of the torso section zone. In alternative embodiments, other cells of layer 20 also inflate and deflate alternately in addition to the alternating of the inflation and deflation of the cells 22 of the torso zone section.

In the illustrative example, the head, torso, and heel section zones of the layer 20 are controlled and operate independently from one another. Further, while the various head, torso, and heel section zones are described herein as including a particular number of laterally-extending cells, it is within the scope of this disclosure to include any number of independently operable zones having any number of interconnected cells, and having cells of any suitable size, shape, or orientation, including cells that extend longitudinally.

The mattress 12 further includes a first air mattress underlay 24 positioned below the layer 20 as well as a second air mattress underlay 26 positioned below the first air mattress underlay 24. Thus, underlay 24 serves as an intermediate layer between layer 20 and underlay 26. Underlay 24 is a single inflatable bladder but has internal walls or connections, such as radio frequency welds between top and bottom sheets of the underlay 24, running in the longitudinal direction of mattress 12 to prevent ballooning of underlay 24. Similarly, underlay 26 is also a single inflatable bladder but has internal walls or connections running in the lateral direction of mattress 12 to prevent ballooning of underlay 26. In the illustrative embodiment, the first air mattress underlay 24 and the second air mattress underlay 26 are interconnected via conduits with each other and with the head section zone of layer 20 and are inflated to the same pressure as the head section zone of the layer 20. The mattress 12 further includes a top coverlet 28 and a bottom coverlet 30 which are coupled together by suitable couplers, such as one or more zippers, to maintain the layer 20 and underlays 24, 26 within an interior region of the mattress 12.

Layer 20 and underlays 24, 26 are inflatable patient support elements of illustrative mattress 12. It should be appreciated that the constructional details of elements 20, 24, 26 are merely illustrative and mattress 12 may have inflatable elements of other shapes, sizes, or orientations. Furthermore, mattress 12 may have non-inflatable patient support elements, such as foam layers, blocks, pads, and the like, as well as mesh materials, gel layers, quilting, and the like, in lieu of or in addition to elements 20, 24, 26. Accordingly, mattresses having no inflatable elements at all are within the scope of this disclosure.

Figure 13:
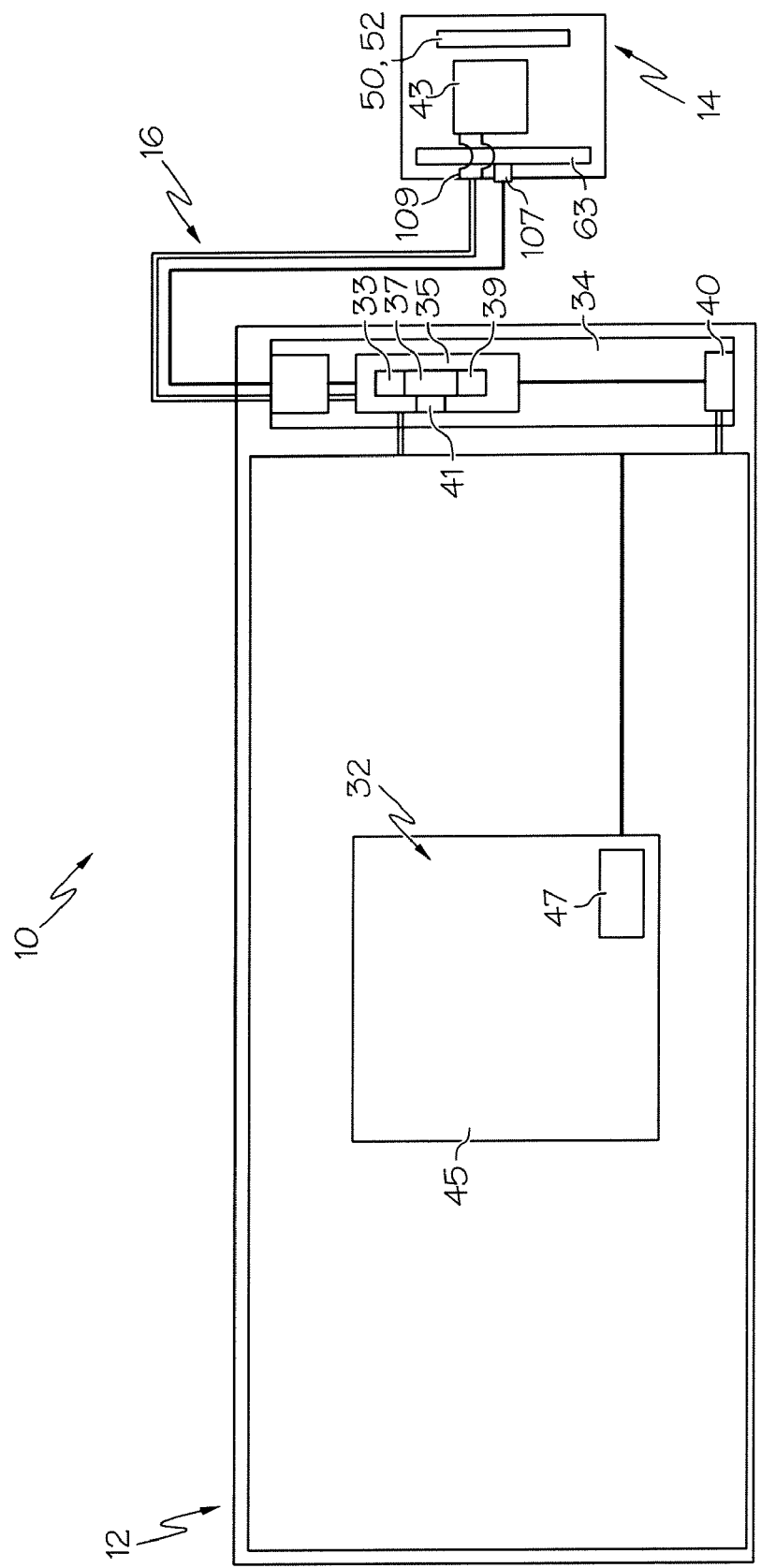
FIG. 13 is a diagrammatic view of the mattress system showing a pressure sensor in a middle region of the mattress and having associated sensor circuitry, a technical box at a foot end of the mattress having valves and associated circuitry, and the control unit with its associated circuitry.

The illustrative mattress 12 further includes a pressure sensor 32 and a technical box 34 containing an air distribution system 35 which includes a set of valves 37, associated circuitry 39, and a manifold assembly 33 in fluid communication with the various cells 22 of layer 20 as well as with the first and second air mattress underlays 24, 26 as shown diagrammatically in FIG. 13. The manifold assembly 33 includes a pneumatic input and a plurality of pneumatic outputs, each of which is associated its own valve of the set of valves 37. In one embodiment, a first valve is in fluid communication with the group of five bladders 22 of the torso section zone while a second valve is in fluid communication with the second group of five bladders 22 of the torso section zone. The first and second sets of bladders 22 in the torso section zone are arranged alternately and the first and second valves 37 are controlled to inflate and deflate the first and second groups of bladders 22 of the torso section zone alternately when mattress system 10 is operating in the alternating pressure mode as dictated by the programming of user interface module 52 as mentioned above. If, on the other hand, user interface module 50 is coupled to the main housing 18 of control unit 14, then the first and second valves 37 are controlled so that all ten of the bladders 22 of the torso zone section remain inflated simultaneously to the same target pressure.

The set of valves 37 includes a third valve in fluid communication with the heel zone of the layer 20 and a fourth valve that is in communication with the head section zone of the layer 20, the first mattress underlay 24, and the second mattress underlay 26. The valves 37 operate to open and close various passageways of the manifold assembly 33 as is appropriate to allow inflation or deflation of the associated groups of bladders of mattress 12. In some embodiments, each of the valves 37 is a three-way valve having an opened position allowing pressurized air to be pumped to the associated bladders 22; a closed position blocking air from being pumped to, and blocking air from escaping from, the associated bladders 22 and underlays 24, 26; and a vent position allowing air to vent from bladders 22 and underlays 24, 26 to atmosphere. In other embodiments, one more of the valves 37 are two position valves and a separate vent valve is provided to vent air from each of the various groups of bladders as needed. In some embodiments, the valves 37 are solenoid valves. However, other suitable valves, such as proportional control valves, may be used if desired. The technical box 34 further houses circuitry 39, referred to herein sometimes as the manifold printed circuit board (PCB) for controlling the operation of the valves 37 within the technical box 34. As is discussed in greater detail below, the manifold PCB is in electrical communication with the control unit 14.

Illustratively, the pressure sensor 32 is positioned within a cut-out section 36 formed in the second air mattress underlay 26 as shown in FIG. 1 while the technical box 34 is positioned at a foot end of the mattress 12 such that foot ends of the air mattress underlays 24, 26 generally abut the technical box but do not extend over the top of the technical box 34. However, the layer 20 (and particularly the heel zone bladders 22 of the layer 20) extends over the technical box 34. When the mattress 12 is assembled, the pressure sensor 32 of the mattress 12 is positioned generally below the torso section zone of the layer 20 in order to sense the pressure exerted by a patient on the torso section zone and provide an output signal to the control unit 14 indicating the sensed pressure.

Mattress 12 includes a cardiopulmonary resuscitation (CPR) assembly that is coupled to the technical box 34 and that includes a rotatable knob 40 that is accessible to the caregiver through an aperture 42 formed in the foot end portion of the bottom coverlet 30. In normal operation, the CPR knob 40 is in a closed position. When the CPR knob 40 is moved manually by a caregiver to an opened position, air rapidly vents through the CPR assembly to atmosphere. In addition, an electrical signal is provided by a switch or other sensor to circuitry 39, the circuitry of control unit 14, and the circuitry of sensor 32 to indicate that the CPR knob 40 has been moved to the opened position. In response to this signal, control unit 14 deactivates operation of the source of a pneumatic pressure 43, such as a compressor, of the control unit 14. A CPR indicator light flashes on the control unit 14 and a CPR alarm sound beeps regularly every 30 seconds to alert the caregiver that the CPR knob 40 has been activated. Once activated, the bladders of layer 20 and underlays 24, 26 quickly deflate to provide a firm surface for performing CPR on the patient lying atop the mattress 12.

Illustratively, the pressure sensor 32 of the mattress 12 comprises a liquid-containing flexible enclosure 45 and associated circuitry 47 as shown in FIGS. 1 and 13. Enclosure 45 and circuitry 47 are both situated in the cut-out section 36 of underlay 26. In some embodiments, the liquid-containing enclosure 45 comprises a bag or bladder filled with a silicon oil, such as polydimethylsiloxane. Circuitry 47 includes a pressure transducer which is exposed to the fluid pressure in the bag via a conduit. The transducer of circuitry 47 detects the pressure exerted upon it by the liquid and relays a pressure signal to the control unit 14 via circuitry 47 and circuitry 39. The pressure sensed by the transducer correlates to the amount of weight and pressure exerted on enclosure 45, which correlates to the weight of the patient on the mattress. As is discussed in greater detail below, circuitry within the control unit 14 operates to establish the target pressures of the zones of layer 20 and underlays 24, 26 and also determines whether one or more zones of the layer 20 are to be inflated or deflated based upon information received from the pressure signal. The principles of operation of the pressure sensor 32 is described in greater detail in U.S. Pat. No. 6,094,762 which is owned by the same assignee as the present application and which is hereby incorporated by reference herein.

As mentioned above, the pressure sensor 32 is positioned below the torso section zone of layer 20. Accordingly, as the patient's torso applies pressure on the mattress 12, this pressure is transferred as a force to the enclosure 45 of pressure sensor 32. The pressure in the enclosure 45 is detected by the transducer of circuitry 47 and a pressure signal is sent to the control unit 14. Circuitry within the control unit 14 then determines whether to vent air from the layer 20 and/or underlays 24, 26 of the mattress 12 or to turn on the pneumatic source 43 within the control unit 14 to inflate the layer 20 and/or underlays 24, 26 in order to reach respective target pressures which are established by control unit 14 based on the signal received from sensor 32. Accordingly, the target pressures of cells 22 of layer 20 and underlays 24, 26 of the mattress 12 are adjusted automatically to accommodate each individual patient's weight and position. In some embodiments, a pressure comparator is provided in circuitry 47 to make a comparison between the pressure in enclosure 45 and the pressure in the head section zone bladders 22 of layer 20 and the underlays 24, 26 and then control unit 14 and valves 37 are operated to equalize the pressure therebetween. In such an arrangement, any additional pressure sensor to sense the pressure in head section zone bladders 22 of layer 22 and underlays 24, 26 may be omitted.

In some embodiments, additional pressure sensors 41 are provided in technical box 34 and are associated with respective pneumatic lines used to inflate layer 20 and underlays 24, 26. The additional pressure sensors detect and communicate the pressure within each zone of the layer 20 and within the underlays 24, 26 to the control unit 14. Such measured pressures are compared with the target pressure values established by the circuitry of control unit 14 based on the pressure signal originating from pressure sensor 32. In other embodiments, technical box 34 has only a single pressure sensor 41 which is coupled sequentially, by appropriate opening and closing of the various valves 37, to each of the zones of layer 22 and to underlays 24, 26 to measure sequentially the pressures in each of the zones.

The data from pressure sensor 32 is used in three distinct operation modes of system 10 including stand-by regulation, patient egress surveillance, and main zone pressure regulation. As is discussed in greater detail below, the stand-by regulation mode means that system 10 operates to achieve a relatively low pressure in the mattress 12 so as to provide a ready-to-use, and yet comfortable, support when the patient is initially placed on the mattress 12. The patient egress surveillance mode means that system 10 operates to monitor the presence and absence of the patient on the mattress 12. The main zone pressure regulation mode means that system 10 operates to control the internal pressures in the bladders 22 of layer 20 and underlays 24, 26. Illustratively, the circuitry 47 of pressure sensor 32 is in electrical communication with the circuitry 39 situated within the technical box 34. As noted above, the circuitry 39 within the technical box 34 is in electrical communication with the control unit 14 via the connector assembly 16.

Figure 16:
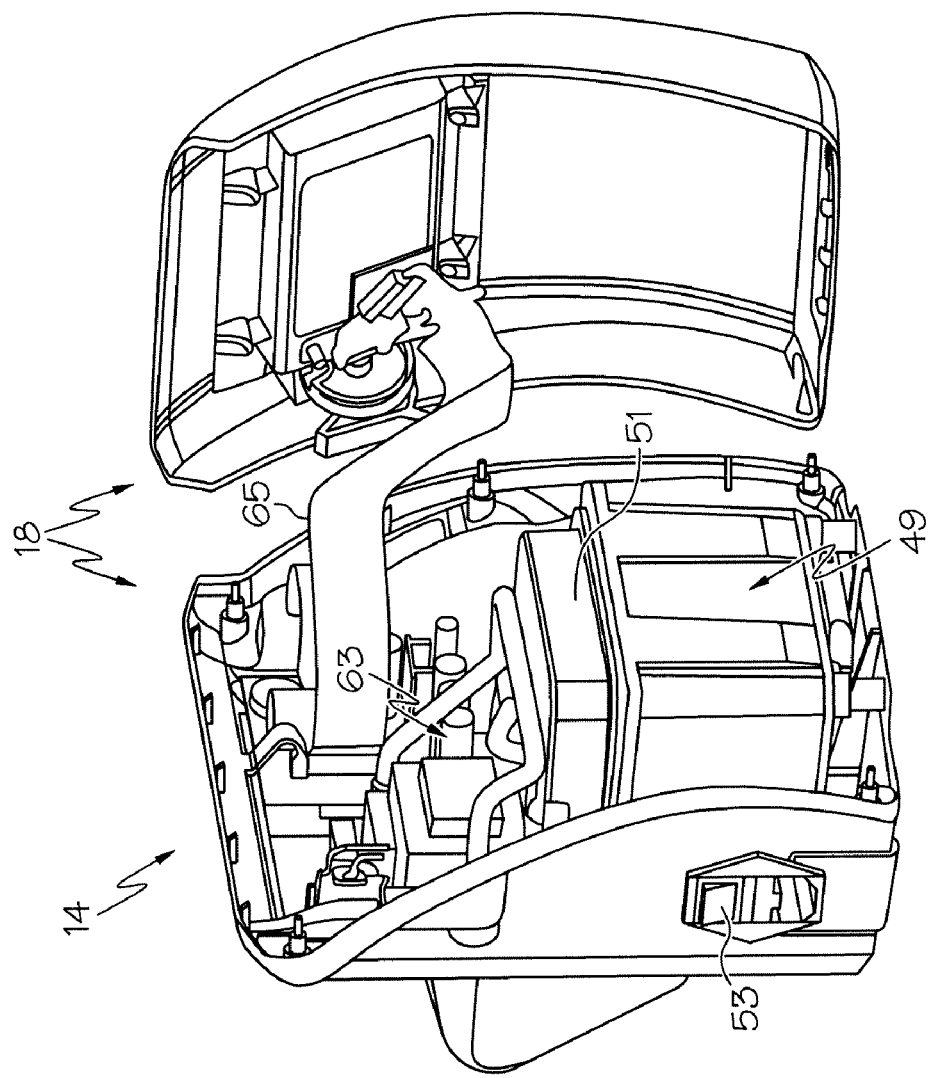
FIG. 16 is a perspective view of the control unit of FIG. 1 showing a front shell of the main housing of the control unit pulled away from a back shell of the main housing, a compressor sub-housing situated in the lower region of the back shell, and circuitry of the control unit situated in the back shell above the compressor sub-housing.

Referring now to FIGS. 2-6, the control unit 14 includes the main housing 18, a source of pneumatic pressure 43 such as a pump, blower, or compressor (shown diagrammatically in FIG. 13) contained within the main housing 18, and first and second user interface modules 50, 52 that are selectively coupleable to the main housing 18. The compressor 43 of the control unit 14 is enclosed in a sub-housing 49, shown in FIG. 16, within the main housing 18 of the control unit 14 to dampen noise while the compressor 43 is running. Power is provided to unit 14 via a power cord 19, shown in FIG. 1, which plugs into unit 14 and into a standard electrical outlet to receive power therefrom. Illustratively, the sub-housing 49 is made of aluminum; however, is should be understood that the sub-housing 49 may be made of other suitable materials to dampen the noise of the compressor 43 contained therein.

Further, an air chamber 51 of the control unit 14 is positioned generally in top region of the compressor sub-housing 49 in order to serve as a pressure reservoir that stabilizes the air flow within the control unit 14 as well as reduce noise output of the control unit 14.

Each of the first and second user interface modules 50, 52 are programmed to control inflation of the layer 20 and/or underlays 24, 26 of the mattress 12 differently in various operational modes of each of interface module 50, 52. Illustratively, the front side of the main housing 18 includes a recess 54 provided therein. The interface modules 50, 52 are each selectively received within the recess 54 and are locked in place by a latch 90 of the control unit 14, as is discussed in greater detail below with regard to FIGS. 7a and 7b. The user interface modules 50, 52 operate as the main caregiver controls of the mattress system 10 while also providing feedback to the caregiver as to the operational status of the system 10. Each of the modules 50, 52 includes circuitry that is programmed with instructions that dictate the operational modes of system 10.

Figure 5:
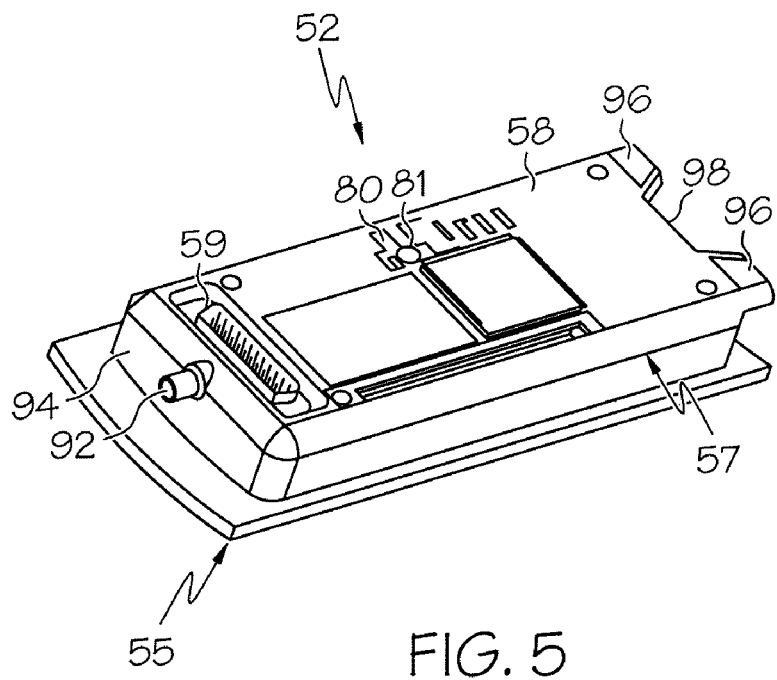
FIG. 5 is a rear perspective of the second user interface module showing a pair of tabs extending from one end of main body of the module and a post extending from an opposite end of the main body of the module and also showing a lock out switch that is accessible on a rear surface of the main body when the module is detached from the control unit.
Figure 6:
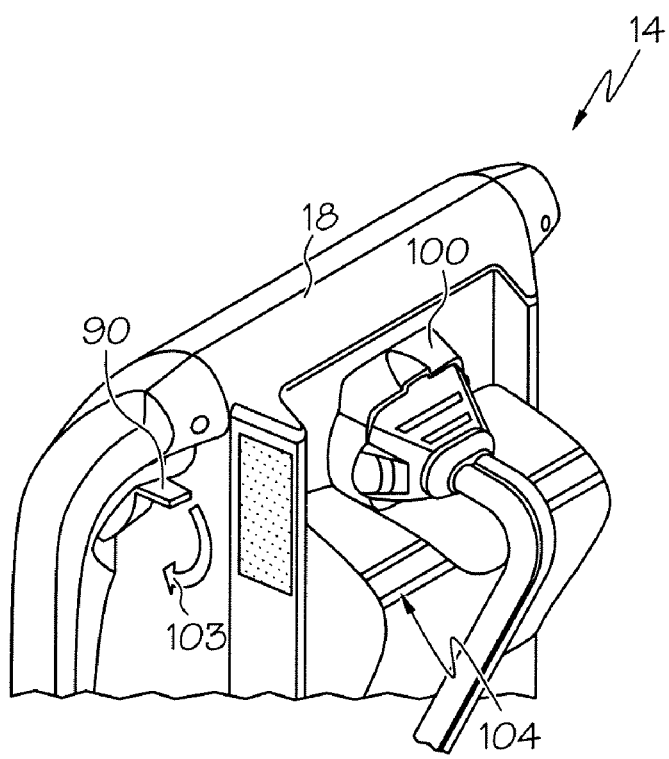
FIG. 6 is rear perspective view of the control unit showing a latch being movable in the direction of the arrow to unlock the user interface module for detachment from the main housing of the control unit.

Referring to FIG. 3, the first user interface module 50 includes a user interface panel 55 having a front surface 56 and a main body 57 that is coupled to the user interface panel 55 and that has a rear surface 58. Illustratively, the first user interface module 50 is a continuous low pressure (CLP) therapy module. The CLP mode of the module 50 is automatically activated when the CLP module 50 is placed in the recess 54 of the control unit 14 and the main switch 53 of control unit 14 (see FIG. 16) is switched on. Illustratively, the CLP module 50 and module 52 each include an electrical connector 59 on the rear surface 58 of the main housing 57 as shown in FIG. 5 with regard to module 52. The electrical connector 59 is coupled to an electrical coupler 61, shown in FIG. 2, within the recess 54 of the control unit 14 to provide electrical communication between the module 50 and internal circuitry 63, shown in FIG. 16, of the control unit 14. A ribbon cable 65, also shown in FIG. 16, interconnects connector 61 and circuitry 63.

During the CLP mode, the ten cells 22 in the torso section of the layer 20 are regulated to the same target pressure (all targets pressures referred to herein have associated tolerance ranges as is well known in the art) as set by the pressure sensor 32. As mentioned above, the three head section cells 22 of the layer 20, the first underlay mattress 24, and the second underlay mattress 26 are fluidly interconnected with each other and are inflated to the same pressure as the cells 22 of the torso section of the layer 20 during the CLP mode. The seven foot section cells 22 of the layer 20 are regulated to a lower target pressure which is determined independently of the rest of the mattress sections.

Various user inputs and indicators are provided on the front surface 56 of the user input panel 55 of the module 50 as shown in FIG. 3. For example, an on/off button 58 is engaged by a user to turn the module 50 on or off. A light indicator 60 illuminates to denote that the module 50 has been turned on. Upon first connecting the control unit 14 to the main power supply, the mattress system 10 operates to automatically inflate the layer 20 and underlays 24, 26 to a maximum inflation pressure value to fully expand the cells 22 and underlays 24, 26. The mattress system 10 then automatically reverts to the therapy mode provided by the selected module 50 or 52 after approximately eight minutes. During start up, the caregiver may press the on/off button 58 twice to override the maximum inflation function, if desired.

An internal pressure indicator provides an indication of the pressure variation in the torso zone of the layer 20. Segments of the light indicator 62 will illuminate as the pressure within the torso zone automatically varies. A maximum inflation (P-max) button 64 is engaged by user to inflate layer 20 and underlays 24, 26 to the maximum inflation pressure at the user's discretion. Thus, the maximum inflation button 64 may then be activated at any time in order to inflate the layer 20 and underlays 24, 26 to the maximum inflation pressure. Oftentimes, for example, a caregiver may use the maximum inflate button 64 in order to provide a firmer patient support surface for patient transfers or bedding changes. Illustratively, pressing the maximum inflation button 64 a second time will immediately end the maximum inflation mode and return the mattress 12 to the therapy mode. The maximum inflation pressure is a target pressure that is typically higher than the pressures to which layer 20 and/or underlays 24, 26 are inflated during other modes of operation of system 10 and it should be understood that layer 20 and underlays 24, 26 are capable of withstanding even higher pressures than the one referred to as the maximum inflation pressure in this disclosure.

Pressing a bed exit alarm button 66 of the user interface module 50 arms or enables a patient egress surveillance system (sometimes referred to herein as a "bed exit system" or "bed exit alarm system" or the like). As is discussed in greater detail below, the pressure sensor 32 of the mattress 12 operates to detect the presence and absence of a patient on the mattress 12 by sending a pressure signal to the control unit 14. Circuitry of the control unit 14 then determines, based upon the value of the pressure signal, whether the patient is present on, or absent from, the mattress 12. The determination regarding the presence of absence of the patient is made by comparing the pressure sensed by sensor 32 with a threshold value. If it is determined that the patient is absent from the mattress 12, an alarm to alert a caregiver is activated if the bed exit alarm system is enabled. The alarm may be a visual alarm such as a light indicator on the module 50 and/or may be an audible alarm such as a beeping noise made by a sound-producing device such as a speaker or piezoelectric buzzer, for example. When the bed exit alarm function is enabled, a light indicator 68 on the module 50 is illuminated.

An alarm silence button 70 of the module 50 may be engaged by a user to temporarily silence any audible alarm associated with the maximum inflation function, the CPR function, a power failure, and/or a mattress malfunction. For example, when one or more of the above-referenced alarms are sounding, the caregiver may press the alarm silence button 70 to temporarily silence the sounding alarm(s). The alarm(s) will then sound again after approximately 10 minutes if the condition causing the alarm is not rectified. The alarm(s) may also be permanently silenced by pressing the alarm silence button 70 until the light indicator 72 flashes. In some embodiments, the alarm silence button 70 also may be engaged by the user to silence a bed exit alarm.

A CPR light indicator 74 of the module 50 flashes when the CPR function, discussed above, is activated. A seat cushion light indicator 76 illuminates when an optional seat cushion (not shown) of the mattress system 10 is being inflated. The indicator 76 turns off after approximately five minutes once the seat cushion is completely inflated. Illustratively, during inflation of the seat cushion, the maximum inflation function is automatically activated without audible indication. The seat cushion inflation may be stopped at any time by pressing the maximum inflation button 64. Once inflated, the seat cushion is disconnected from control unit 14 and remains inflated for use on a wheel chair or other type of seating surface. A valve coupled to the seat cushion may be open to allow deflation of the seat cushion to atmosphere.

A safety lock-out light indicator 78 of the module 50 illuminates whenever the user interface module 50 is locked-out to prevent a patient or caregiver from adjusting the settings. Illustratively, as shown in FIG. 5 with regard to module 52, the rear surface of the module 50 and the module 52 each includes a lock-out switch 80. The caregiver may move the lock-out switch 80 to an activated position in order to lock-out the controls of the module 50 or the module 52, as the case may be, to prevent a patient or other caregiver from tampering with the particular settings of the module 50, 52, thereby to prevent intentional or unintentional changes in the operating mode of system 10. Illustratively, the lock-out switch 80 is located on the rear surface 58 of the module 50, 52 and is, therefore, generally inaccessible by the patient. The safety lock-out indicator 78 is illuminated when the lock-out switch 80 has been activated. Illustratively, the safety lock-out indicator light 78 will then flash in the event of a control button being pressed in order to signal that the user interface is locked-out.

To unlock the lock-out function, the caregiver removes the module 50 from the housing 18 of the control unit 14 and moves the lock-out switch 80 to the deactivated or unlocked position. Alternatively, the caregiver may temporarily unlock the lock-out function by removing the module 50 from the housing 18 and pressing a lock-out button 81 adjacent the switch 80. Illustratively, pressing the lock-out button 81 (while maintaining the switch 80 in the activated position) operates to deactivate the lock-out function for a predetermined period of time, such as 20 seconds, for example. This function allows the user then to resecure the module 50 to the housing 18 and manipulate the controls of the module 50 without having to again remove the module 50 from the housing to reinitiate the safety lock-out function. Once the caregiver has manipulated the controls of the module 50, the lock-out function will be automatically reactivated once the predetermined period of time has elapsed.

A power failure light indicator 82 illuminates when the control unit 14 is disconnected from the main power supply or in the event of a power failure. The power failure light indicator 82 will also illuminate during transport. A mattress malfunction light indicator 84 of module 50 illuminates in the event of a pressure fault and a continuous low pressure (CLP) therapy indicator 86 of module 50 illuminates to indicate that CLP therapy is being used.

Illustratively, as noted above, an audible alarm is sounded, as well as a visual indicator being illuminated, when the maximum inflation function has been activated, when the CPR function has been activated, when a patient has exited the bed (assuming the bed exit alarm system is enabled), when the control unit 14 has been disconnected from the main power supply or when a power failure has occurred, and when a mattress defect is detected.

Referring now to FIG. 4, the second user interface module 52 similarly includes the user interface panel 55 having the front surface 56 and the main body 57 having the rear surface 58. Illustratively the second user interface module 52 is an alternating pressure (AP) therapy module. The AP therapy mode is automatically activated when the AP module 52 is placed within the recess 54 of the main housing 18 of the control unit 14. Illustratively, the AP mode affects the ten cells 22 within the torso section zone of the layer 20 to sequentially inflate and deflate every other cell 22 within the torso section zone. Accordingly, none of the three head section cells 22 and none of the seven heel section cells 22 are alternately inflated and deflated in the illustrative embodiment, but may do so in other embodiments.

As noted above, the pressure in the torso section cells 22 is controlled by the pressure sensor 32. Illustratively, the AP mode may be described in three phases. In the first phase, five non-adjacent cells 22 (forming a first AP zone of cells) in the torso section zone of the layer 20 are deflated. This deflation takes approximately four minutes. In the second phase, the pressure in all the cells 22 within the torso section is the same (i.e., at a continuous low pressure). The duration of the second phase is approximately 1 minute. The purpose of the second phase of the AP therapy mode is to enhance patient comfort by providing a soft surface between the deflated phases. In the third phase, the other five non-adjacent cells 22 (forming a second AP zone of cells) in the torso section zone of the layer 20 are deflated. Similar to the first phase, the third phase lasts approximately four minutes. A similar discussion of the AP mode is presented above.

Various user inputs and indicators are provided on the front surface 56 of the user input panel 55 of the module 52. Illustratively, many of these user inputs are the same as those discussed above with respect to the first user interface module 50. As such, like reference numerals have been used to denote like inputs and/or indicators. However, rather than including the CLP indicator 86 of the module 50, the module 52 includes an alternating pressure (AP) therapy indicator 88 to indicate that AP therapy is being used.

Although the CLP user interface module 50 and the AP user interface module 52 are provided in the illustrative examples, it is within the scope of this disclosure for the mattress system 10 to include other user interface modules that are selectively coupleable with the control unit 14 as well. For example, a rotation therapy user interface module may provide a continuous lateral rotation therapy (CLRT) function and a low air loss user interface module may provide a low air loss function for cooling the patient and/or wicking moisture away from the patient. Of course, it should be understood that any number of user interface modules having any number of therapy functions may be provided for use with the control unit 14 and mattress 12 of the mattress system 10. Further, it is within the scope of this disclosure to include more than one therapy function on a single user interface module. For example, while each of the CLP and AP modules 50, 52 are dedicated to a single therapy, a single user interface module may be provided which includes both CLP and AP therapies. Accordingly, any number and any combination of desired therapies may be provided on a single user interface module. Each user interface module includes circuitry that is programmed to implement its associated functionalities. Thus, the programming of the various types of modules is different. This provides a cost savings to healthcare facilities because, to achieve different types of patient therapies, only the associated user interface modules need to be purchased rather than having to purchase an entirely different mattress system.

Each of the user interface modules 50, 52 further includes a locking post 92 extending from a first end of 94 the main body 57 of the respective module 50, 52, as shown in FIGS. 3 and 4. Referring now to FIG. 5, a pair of tabs 96 of each user interface module 50, 52 extend outwardly from a second end 98 of the main body 57 of the respective module 50, 52. Thus, post 92 and tabs 96 extend from main body 57 in opposite directions. As is discussed below, the locking post 92 and tabs 96 are used to secure the respective modules 50, 52 within the recess 54 formed in the main housing 18 of the control unit 14.

Figure 7A:
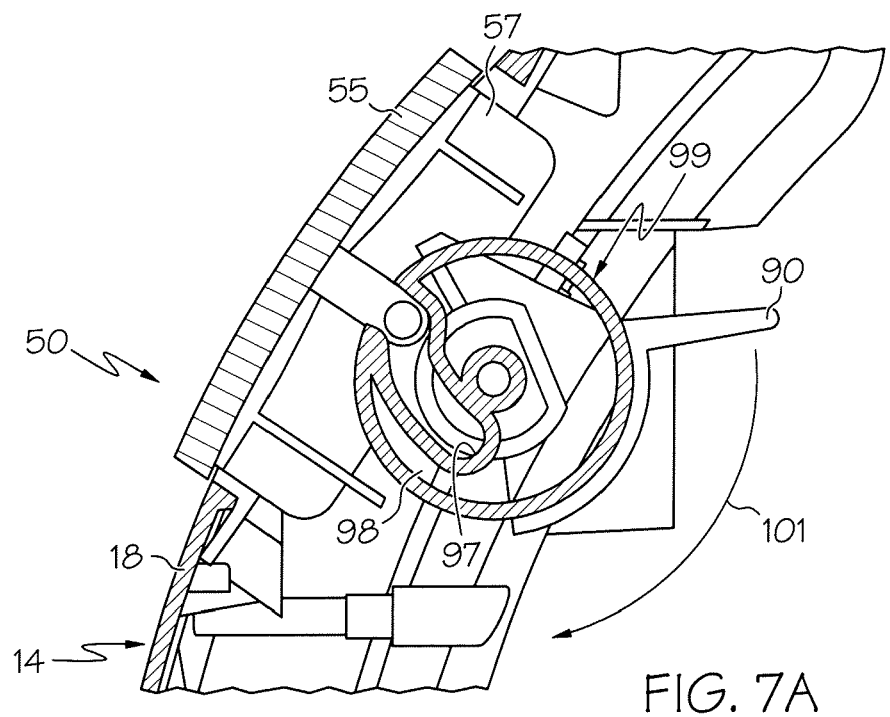
FIG. 7a is a side elevation view of the control unit of FIG. 6, with portions broken away, showing the latch in an unlocked position showing the post situated at an open end of a slot formed in a hook or cam of the latch.

As noted above, the user interface modules 50, 52 may be selectively attached to and removed from the main housing 18 of the control unit 14. In order to attach one of the first and second user interface modules 50, 52 to the main housing 18 of the control unit 14, the caregiver slides the pair of tabs 96 of the selected module 50 or 52 into corresponding slots 67, shown in FIG. 2 (in phantom), formed in the main housing 18 of the control unit 14. In the illustrative embodiment, the slots of the housing 18 are formed in a side wall of housing 18 defining part of the recess 54. Once the tabs 96 of the selected module 50 or 52 are received within the corresponding slots of the housing 18, the main body 57 of the selected module 50 or 52 may further moved into the recess 54 such that the locking post 92 is received within a slot 97 defined by hook portion 98 of a pivotable cam 99 coupled to the latch 90 to further secure the selected module 50 or 52 within the housing 18. Illustratively, as shown in FIGS. 7a and 7b, movement of the latch 90 in a first direction 101 operates to rotate the cam 99 in a clockwise direction such that the slot 97 of the hook portion 98 captures the post 92 of the selected module 50 or 52 therein (as shown in FIG. 7b).

Figure 7B:
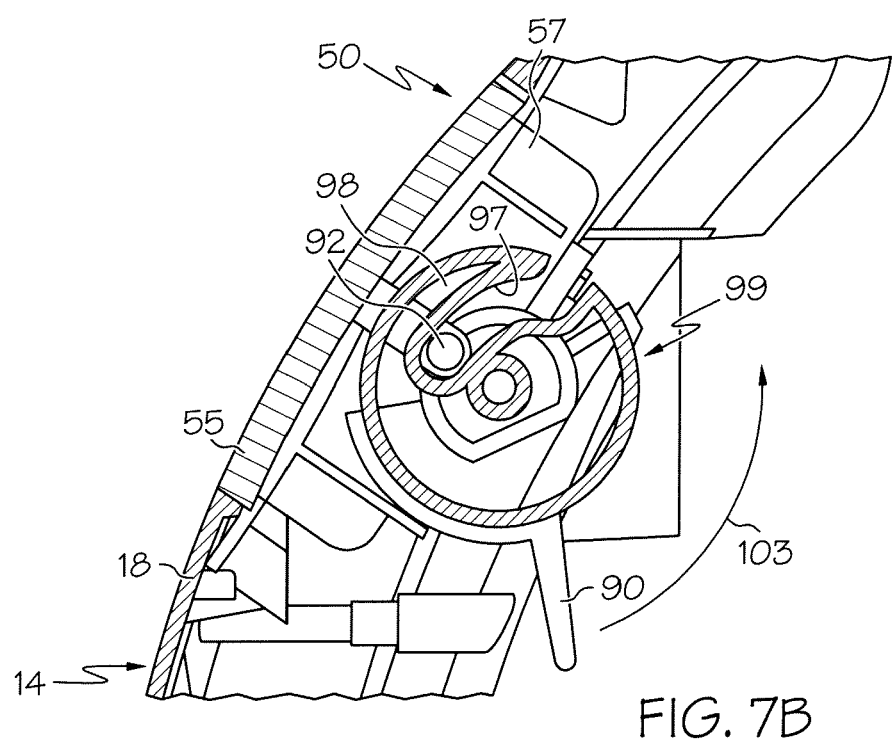
FIG. 7b is a side elevation view, similar to FIG. 7a, showing the latch in a locked position such that the post of the user interface module is captured within the slot of the hook.

In order to remove one of the first and second user interface modules 50, 52 from the control unit 14, the caregiver may rotate the latch 90 located at the rear side of the control unit housing 18 in direction 103 shown in FIG. 7b from a first, locked position to a second, unlocked position. Illustratively, movement of the latch 90 in direction 103 operates to rotate the cam 99 in a counterclockwise direction such that the post 92 of the selected module 50 or 52 becomes disengaged from the slot 97 of the hook portion 98 (as shown in FIG. 7a). When the latch 90 is in the second, unlocked position, hook 98 of the cam 99 is disengaged from the post 92 of the selected module 50 or 52 to allow the caregiver to remove the particular user interface module 50 or 52 from the main housing 18 of the control unit 14.

The shape of slot 97 is such that when latch 90 is rotated in direction 101, with hook portion 98 capturing post 92, post 92 is pulled generally radially inwardly toward the pivot axis of latch 90 to firmly seat the associated module 50, 52 against the main housing 18 and to pull the electrical connectors 59, 61 together. On the other hand, when latch 90 is rotated in direction 103, with hook portion 98 capturing post 92, post 92 is pushed generally radially outwardly way from the pivot axis of latch 90 to unseat the associated module 50, 52 from housing and to push the electrical connectors 59, 61 apart. After being unseated in this manner, the module 50, 52 is far enough away from main housing 18 to provide space for a user to grasp the module 50, 52, as shown in FIG. 7a with regard to module 50, and completely detach it from housing 18.

Figure 8:
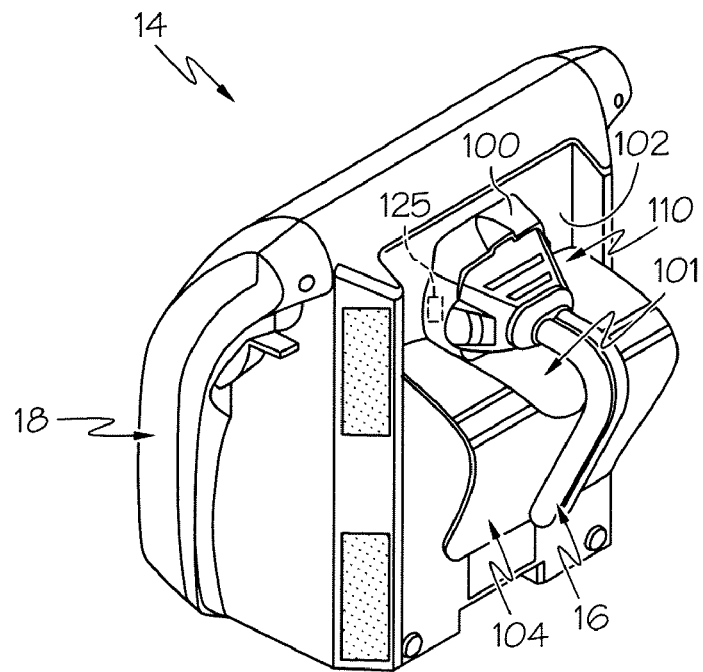
FIG. 8 is a rear perspective view of the control unit similar to FIG. 6 showing a dual mode plug of the connector assembly coupled to a socket provided in a rear wall of the main housing of the control unit and showing a coupling hook having a cut out beneath the dual mode plug.

Referring now to FIG. 8, the control unit 14 further includes a socket 100 formed in a rear wall 102 of the main housing 18 as well as a bracket assembly or coupling hook 104 coupled to the rear side 102 of the main housing 18. As is discussed in greater detail below, the socket 100 of control unit 14 receives a dual mode plug 110 of the connector assembly 16 therein. Illustratively, the coupling hook 104 is positioned below the socket 100 of the main housing 18 and is provided to allow a caregiver to hang the control unit 14 on a footboard or side rail of a bed frame, for example. Hook 104 has a cutout 101 to accommodate the dual mode plug 110 and a user's fingers when attaching the connector assembly 16 to, or detaching the connector assembly 16 from, housing 18. The control unit 14 also includes rubber pads (not shown) on a bottom surface of the main housing 18 in order to enable the control unit 14 to stand on a hard surface as well.

Figure 9:
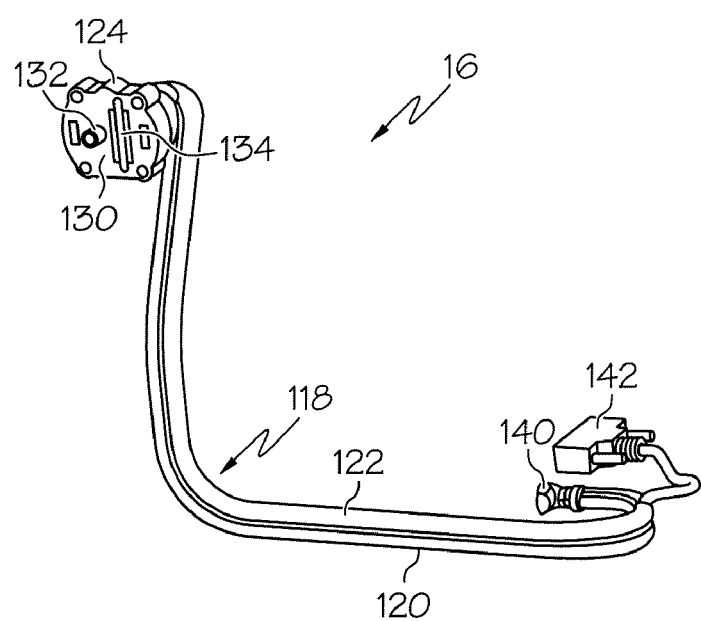
FIG. 9 is a perspective view of the connector assembly showing a dual lumen hose having one end coupled to the dual mode plug and having pneumatic and electrical couplers at an opposite end thereof.

Referring now to FIGS. 9-12, the connector assembly 16 of the mattress system 10 provides a pneumatic and electrical connection between the control unit 14 and the mattress 12. The connector assembly 16 includes a dual lumen hose 118 including a pneumatic line 120 for communication of pneumatic pressure from the control unit 14 to the mattress 12 and an electrical line 122 that serves as an electrical conduit through which electrical conductors are routed between the control unit 14 and the mattress 12. Illustratively, the pneumatic line 120 and the electrical line 122 are connected to each other and positioned side-by-side along a majority of the length of the lines 120, 122, as shown in FIG. 9, for example.

The connector assembly 16 further includes the dual mode plug 110 at a first end of the dual lumen hose 118. The dual mode plug 110 is received within the socket 100 of the main housing 18 in order to provide a substantially simultaneous pneumatic and electrical connection with the control unit 14. Illustratively, the dual mode plug 110 includes a plug housing 124 and two latch members 126 coupled to respective sides of the plug housing 124. In particular, the plug housing 124 includes a pair of recesses 127 formed in each side of the plug housing 124 such that a portion of each latch member 126 is received within a respective recess 127. Each of the latch members 126 are movable between a first position locking the dual mode plug 110 to the main housing 18 of the control unit 14 and a second position unlocking the dual mode plug 110 from the main housing 18 of the control unit 14. Illustratively, the latch members 126 are spring-biased toward the first position by respective springs 128, shown in FIG. 10. Further, in order to move the latch members 126 between the first and second positions, a caregiver squeezes each latch member 126 in a direction generally toward the plug housing 124 and further within the respective recesses 127.

Figure 10:
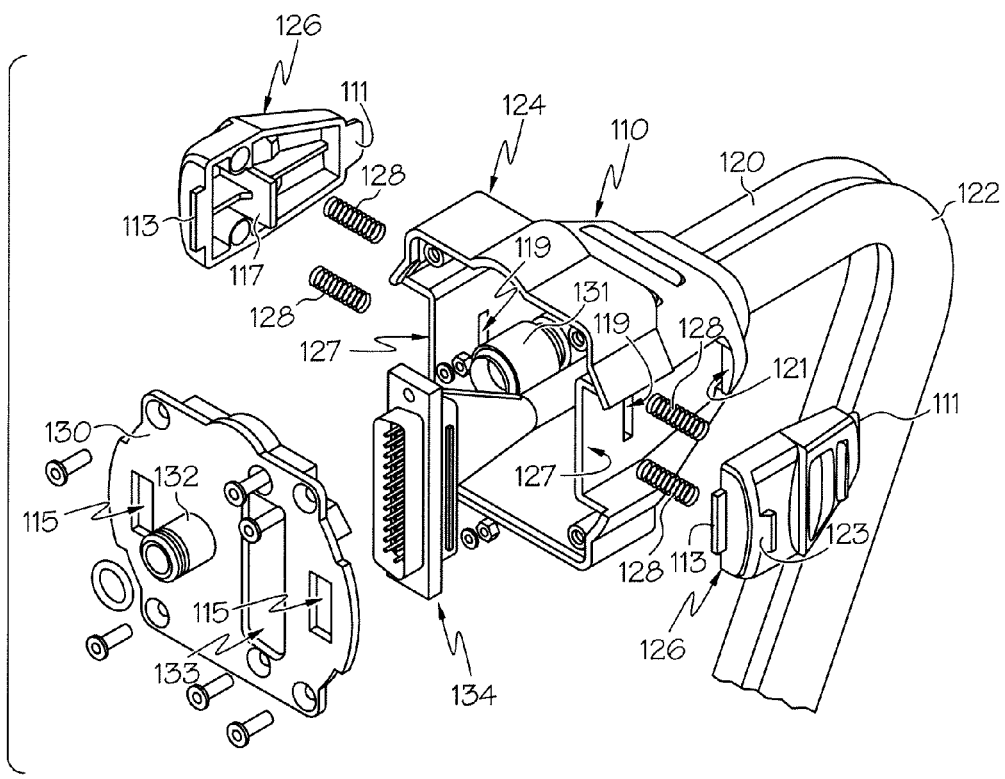
FIG. 10 is an exploded view of the dual mode plug at the end of the connector assembly that couples to the control unit.

Referring still to FIG. 10, the dual mode plug 110 further includes a front wall 130 coupled to the housing 124, a pneumatic coupler 132 extending away from the front wall 130, and an electric coupler 134 that extends beyond front wall 130 through an aperture 133 formed therein. A first end of each of the electrical conductors routed through line 122 is coupled to, and terminates at, electrical connector 134. The control unit 14 includes an electrical connector 107 (shown diagrammatically in FIG. 13) within the socket 100 which is in communication with the internal circuitry 63 control housing 14 and a pneumatic port 109 (also shown diagrammatically in FIG. 13) within the socket 100 which is in communication with the compressor 43 of the control unit 14. Accordingly, when the dual mode plug 110 is received within the socket 100 of the control unit 14, the pneumatic coupler 132 of the plug 110 is coupled to the pneumatic port 109 of the control unit 14 and the electric coupler 134 of the plug 110 is coupled to the electrical connector 107 of the control unit 14. Further, the dual mode plug 110 is configured so that the electrical and pneumatic connections between the connector assembly 16 and the control unit 14 are made substantially simultaneously.

A check valve 131 is provided within housing 124 of plug 110 and is in pneumatic communication with port 132. When plug 110 is coupled to socket 100 and compressor 43 is operated, the check valve 131 is opened to allow pressurized air to move through pneumatic line 120. When plug 110 is disconnected from socket 100, check valve 131 is closed to prevent air from escaping from mattress 14 through connector assembly 16.

Latch members 126 each have a rearwardly projecting tab 111 that is captured within a rear pocket 121 of the respective recess 127 and a forwardly projecting tab 113 that extends through a respective aperture 115 of front wall 130. Apertures 115 are oversized in the lateral direction to allow movement of tabs 113 therein when latch members 126 move between the first and second positions. Each latch member 126 also has a laterally inwardly projecting tab 117 that is received in an associated slot 119 formed in a respective side of housing 124. Receipt of tabs 111, 113 in the associated pockets 121 and apertures 115 retains latch members 126 in place within recess 127, whereas receipt of tabs 117 in slots 119 guides the lateral movement of latch members 126. Each of latch members 126 further has a laterally outwardly projecting tabs 123 that is received in associated tab-receiving recess or pocket 125, shown in FIG. 8 (in phantom), formed in the sidewalls of socket 100. Receipt of tabs 123 in recesses 125 locks plug 110 to the socket 100 of the housing 18 of the control unit 14. When latch members 126 are squeezed toward housing 124 of plug 110, tabs 123 are withdrawn from recesses 125, thereby allowing plug 110 to be disconnected from socket 100.

Figure 11:
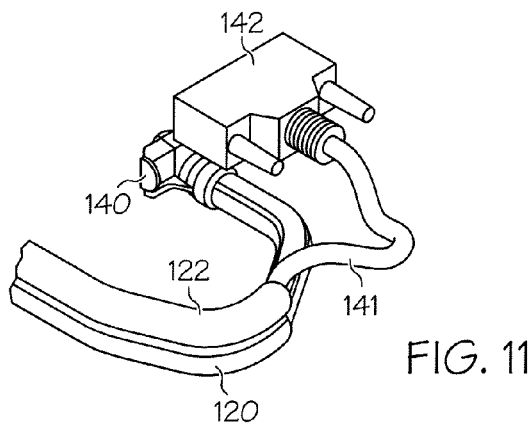
FIG. 11 is an enlarged perspective view of the end of the connector assembly that couples to the mattress of the mattress system.
Figure 12:
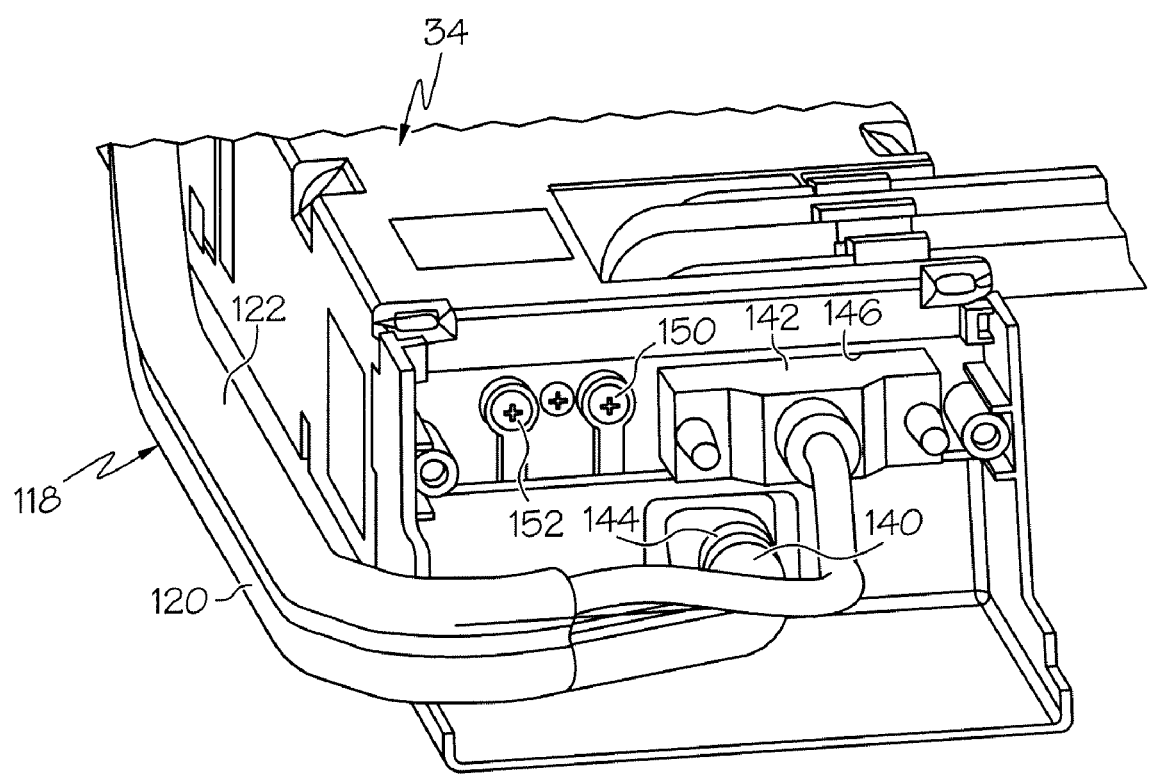
FIG. 12 is an enlarged perspective view showing the pneumatic and electrical couplers of the connector assembly coupled to mating pneumatic and electrical connectors, respectively, included in the mattress.

Referring now to FIGS. 9 and 11, the connector assembly 16 further includes a pneumatic coupler 140 mounted to the second end of the pneumatic line 120 and an electrical connector 142 mounted to an end of a cable 141 of the electrical conductors which exit from the second end of the electrical line 122. As shown in FIG. 12, the pneumatic coupler 140 is coupled to a pneumatic port 144 of the mattress 12. Specifically, the technical box 34 includes the pneumatic port 140 which is in pneumatic communication with the inflatable layer 20 and underlays 24, 26 of the mattress 12 via the manifold assembly 35 within the technical box 34. Further, the electrical connector 142 of the connector assembly 16 is coupled to an electrical connector 146 of the technical box 34 of the mattress 12. The electrical connector 146 of the mattress 12 is in electrical communication with the electrical circuitry 39, 47 within the mattress 12. Further illustratively, the technical box 34 includes a first pressure test port 150 for checking the pressure in the torso zone of the layer 20 and a second pressure test port 152 for checking the pressure in the heel zone of the layer 20. Pressure transducers 41 of technical box 34 are coupled electrically to test ports 150, 152 to provide feedback information regarding the pressure within an associated zone of mattress 14.

In operation, air enters the control unit 14 through an air filter (not shown) within the control housing 18 of the control unit 14. The air then travels into the compressor inlet. Upon exiting the compressor 43, the air travels through check valve 131 and the pneumatic line 120 of the connector assembly 16 and into the manifold assembly 35 located in the technical box 34 within an interior region of the mattress 12. The air is then dispatched through valves 37 into the various inflatable mattress layers including the layer 20, the first air mattress underlay 24, and the second mattress underlay 26. In the illustrative embodiment, the check valve 131 located inside plug 110 of the connector assembly 16 provides approximately four hours of inflation of the mattress 12 in the event the control unit 14 is disconnected from the main power supply or if the dual lumen hose 118 is disconnected from the control unit 14.

Figure 14:
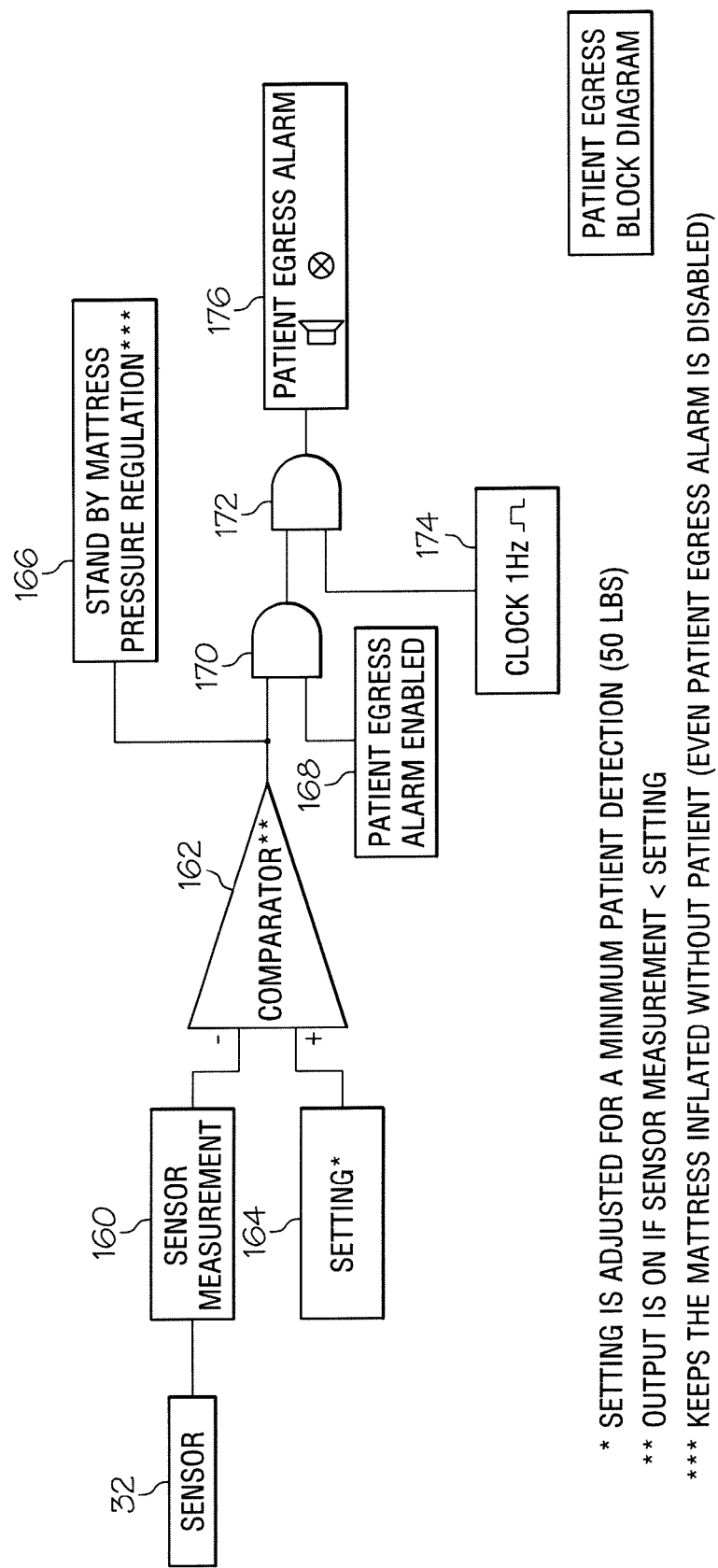
FIG. 14 is a block diagram showing the logic implemented by the circuitry of the mattress system to control a bed exit alarm.

As mentioned above, each of modules 50, 52 is programmed to provide system 10 with a bed exit alarm function. FIG. 14 is a diagram which illustrates the logic of the bed exit alarm function of system 10. Sensor 32 provides a signal to circuitry 47 which measures the pressure exerted on sensor 32 as indicated at block 160. A comparator 162 receives the pressure measurement signal and also receives a threshold setting signal which is represented by block 164 in FIG. 14. In one embodiment, the threshold setting is established for a minimum patient weight of fifty pounds but, in other embodiments, other threshold settings may be established at the discretion of the system programmer or designer.

If the pressure measurement signal is less than the threshold value signal, which is an indication that the patient has exited the mattress 14, then the output of comparator 162 is on (e.g., a high logic state), otherwise the output of comparator 162 is off (e.g., a low logic state). If the comparator is turned on, then system 10 automatically operates in the stand by mattress pressure regulation mode in which layer 20 and underlays 24, 26 are controlled to reduced pressure settings as indicated at block 166. If the bed exit or patient egress alarm is enabled, as indicated at block 168 and the comparator is on, then the output of an AND gate 170 is on. The output of AND gate 170 is input to another AND gate 172 which has a second input from a 1 Hertz (Hz) clock 174. Thus, if the output of AND gate 170 is on, then the output of AND gate 172 will be a 1 Hz signal that is fed to patient egress alarm indicator as indicated at block 176.

As mentioned above the bed exit alarm may include a visual indicator, such as a light emitting diode (LED) and/or a sound producing device, such as a speaker or buzzer. In the illustrative embodiment, the 1 Hz signal being output from AND gate 172 will cause the visual indicator to flash at a rate of 1 Hz and will cause the sound producing device to beep at a rate of 1 Hz. Although, logical AND gates 170, 172 are used in FIG. 14 to explain the operation of the bed exit alarm function of system 10, it should be appreciated that the logical AND conditions may be implemented by software rather than by use of discrete logic gates, but use of discrete logic gates is within the scope of the disclosure as well.

Figure 15:
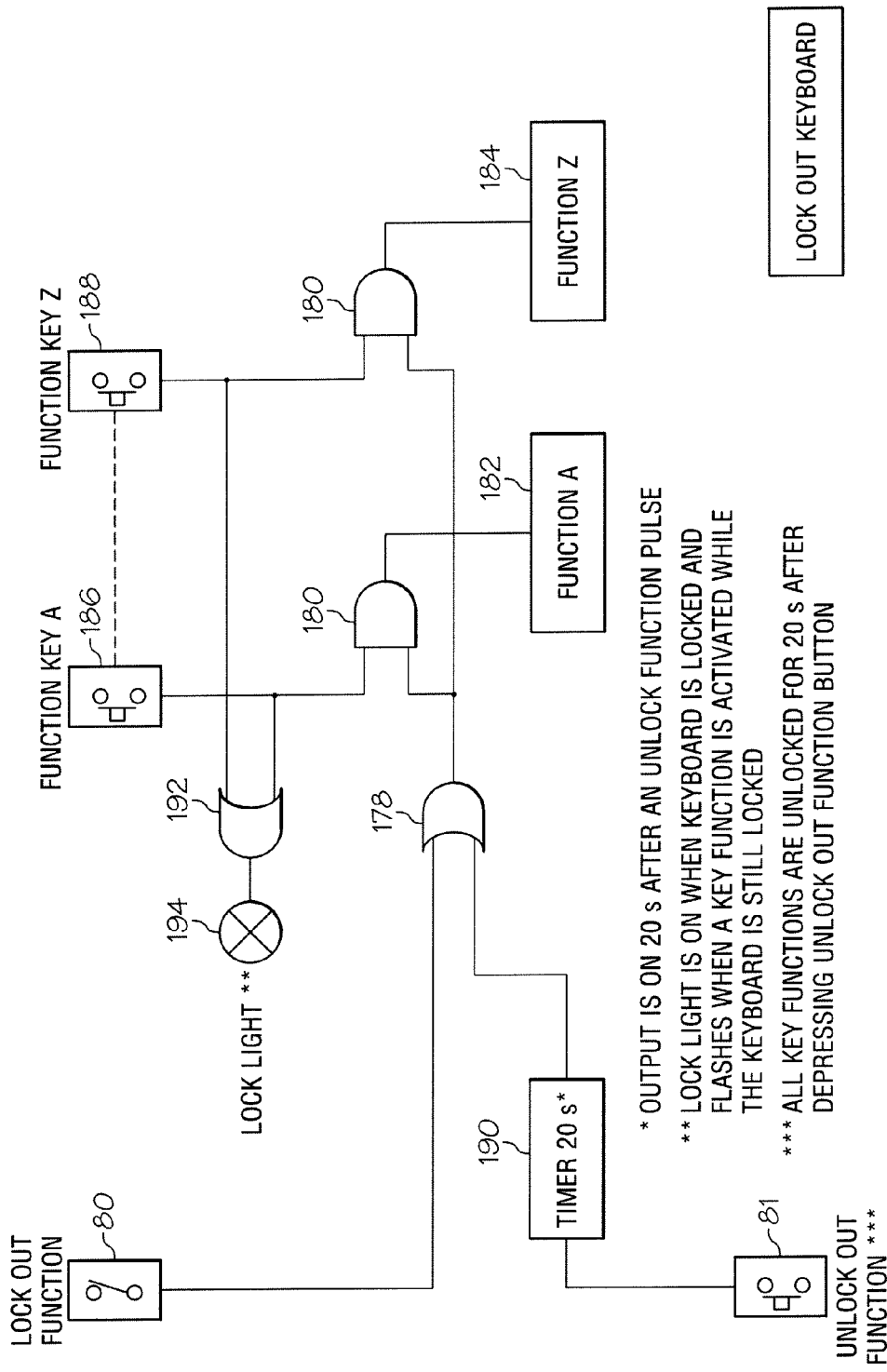
FIG. 15 is a block diagram showing the logic implemented by the circuitry of the mattress system to control a lock out function provided in each of the user interface modules.

As mentioned above, each of modules 50, 52 includes lock-out switch 80 and lock-out button 81 which are used to lock out various functions of the modules 50, 52 and to unlock the functions. FIG. 15 is a diagram which illustrates the logic of the lock out function of system 10. When switch 80 is in its position enabling various functions of system 10, an output of an OR gate 178 is turned on (i.e., a high logic state) and is coupled to the input of a set of AND gates 180, each of which is associated with a respective function as indicated generically at a "function A" block 182 and at a "function Z" block 184 in FIG. 15. A "function key A" switch 186 is coupled to the input of the AND gate 180 associated with function A and a "function key Z" switch 188 is coupled to the input of the AND gate 180 associated with function Z. Function A and function Z are intended to generically represent the functions of system 10. The dotted lines appearing in FIG. 15 between switches 186, 188 and between the output of OR gate 178 and the AND gate associated with function Z are intended to convey the notion that additional functions may be controlled in the same manner as the two that are illustrated.

When the output of OR gate 178 is on, which occurs when system 10 is enabled, and button 186 or button 188 is pressed, the associated AND gate has two high logic states at its input resulting in its associated output being turned on (i.e., a high logic state) to signal the operation of the associated function A or function Z. If switch 80 is in its position disabling or locking out the various functions of system 10, and assuming button 81 is not pressed, then both inputs to OR gate 178 are at low logic states and the output of OR gate 178 is off (i.e., a low logic state) resulting in the output of the associated AND gates 180 being turned off, regardless of whether either of buttons 186, 188 is pressed.

If switch 80 is in its position locking out the various functions of system 10 and switch 81 is pressed, then a twenty second timer is activated, as indicated at block 190, resulting in a high logic state being applied at one of the inputs of OR gate 178 for twenty seconds, thereby turning the output of OR gate 178 on, thereby enabling the various functions of system 10 for twenty seconds. During this twenty period, switches 186, 188 may be pressed to operate the associated function 182, 184. After the expiration of the twenty second timer, the OR gate 178 once again receives two low logic inputs which turns off the output of the OR gate 178 thereby locking out the functions of system 10.

Switches 186, 188 are coupled to the inputs of an OR gate 192 as shown in FIG. 15. The output of OR gate 192 is coupled to a lock light 194. Lock light 194 is turned on by OR gate 192 when switch 80 is in its position locking out the functions of system 10 and lock light 194 flashes if either of switches 186, 188 is pressed when system 10 is locked out. Although, logical AND gates 180 and logical OR gates 178, 192 are used in FIG. 15 to explain the operation of the lock out function of system 10, it should be appreciated that the logical AND and logical OR conditions may be implemented by software rather than by use of discrete logic gates, but use of discrete logic gates is within the scope of the disclosure as well.

Although certain illustrative embodiments have been described in detail above, variations and modifications exist within the scope and spirit of this disclosure as described and as defined in the following claims.

The invention claimed is:

1. A mattress system comprising
a mattress having at least one inflatable bladder, and
a control unit comprising a main housing, a source of pneumatic pressure carried by the main housing and operable to inflate the at least one inflatable bladder via a pneumatic path, a bracket that extends away from a rear side of the main housing and that is configured to permit the control unit to be hung on a footboard of a bed, and a plurality of user interface modules that are interchangeably receivable at least in part within a recess provided in a front side of the main housing, each user interface module being programmed to control inflation of the at least one air bladder differently in at least one operational mode of each of the plurality of user interface modules, the control unit having a latch mounted to the main housing and movable relative to the main housing, the control unit having a first electrical connector within the recess and each user interface module having a second electrical connector, wherein movement of the latch relative to the housing by a user from a first position to a second position results in the selected user interface module received in the recess being mechanically locked to the main housing by the latch and results in the first and second electrical connectors being pulled together, wherein the recess and the plurality of user interface modules are sized such that only one interface module at a time is received within the recess and wherein the user interface module occupying the recess is excluded from the pneumatic path through which the at least one bladder is inflated.

2. The mattress system of claim 1, wherein the plurality of user interface modules include an alternating pressure module and a continuous low pressure module.

3. The mattress system of claim 1, wherein the plurality of user interface modules include a rotation therapy module.

4. The mattress system of claim 1, wherein each of the plurality of user interface modules has user inputs that are used to change a mode of operation of the associated user interface module.

5. The mattress system of claim 1, wherein as the latch is moved from the second position to the first position, the first and second electrical connectors are pushed apart and the selected one of the plurality of user interface modules is moved out of the recess by a sufficient amount to permit a user to grasp the selected user interface module to detach the selected user interface module from the main housing.

6. The mattress system of claim 5, wherein the latch has a hook and each of the user interface modules has a post that is captured by the hook when the associated user interface module is locked to the main housing by the latch.

7. The mattress system of claim 6, wherein the main housing has at least one slot and each of the plurality of interface modules has at least one tab that is received in the slot provided in the main housing when the associated user interface module is coupled to the housing.

8. The mattress system of claim 7, wherein each of the user interface modules comprises a main body, the post and the at least one tab of each of the plurality of user interface modules are located on opposite ends of the associated user interface modules, and the post and the at least one tab of each of the plurality of user interface modules extend away from the associated main body in opposite directions.

9. The mattress system of claim 1, wherein the recess is provided in a curved front wall of the main housing.

10. The mattress system of claim 1, wherein the second electrical connector of each user interface module is located on a rear surface of the respective user interface module.

11. The mattress system of claim 1, wherein at least one of the plurality of user interface modules has a lockout switch that is usable to lockout at least one operational mode of the associated user interface module.

12. The mattress system of claim 11, wherein the lockout switch is located adjacent a surface of the associated user interface module that is inaccessible to a user when the associated user interface module is coupled to the main housing.

13. The mattress system of claim 12, wherein the lockout switch is located adjacent a back surface of the associated user interface module.

14. The mattress system of claim 12, wherein the operational mode that the lockout switch is usable to lockout comprises a maximum inflation mode.

15. The mattress system of claim 1, wherein at least one of the plurality of user interface modules includes inputs that are engageable to enable a bed exit alarm system of the control unit.

16. The mattress system of claim 15, wherein the bed exit alarm system receives an input signal from the mattress indicative of a pressure sensed by a pressure sensor situated in an interior region of the mattress.

17. The mattress system of claim 1, wherein the source of pneumatic pressure of the control unit comprises an air compressor within a noise-dampening housing that is situated within an interior region of the main housing.

18. The mattress system of claim 17, wherein the noise-dampening housing has an air chamber that serves as a pressure reservoir which stabilizes air flow to the at least one air bladder of the mattress.

19. The mattress system of claim 1, wherein the mattress has at least one valve located within an interior region of the mattress and the valve is opened and closed to control pressure in the at least one inflatable bladder in a manner dictated by the programming of the selected user interface module that is coupled to the main housing.

20. The mattress system of claim 1, wherein the mattress has at least one pressure sensor is situated within an interior region of the mattress and an output signal from the at least one pressure sensor is communicated to the selected user interface module that is coupled to the main housing.

21. The mattress system of claim 1, wherein at least one cardiopulmonary resuscitation (CPR) input is coupled to the mattress and is movable mechanically to deflate the at least one air bladder of the surface, wherein movement of the CPR input results in a CPR signal being communicated to the selected user interface module that is coupled to the main housing, and the selected user interface module deactivates operation of the source of pneumatic pressure in response to receiving the CPR signal.

22. The mattress system of claim 1, wherein each of the plurality of user interface modules includes at least one visual indicator that is operable to provide visual indication of the operational status of the mattress system.

* * * * *